(12) United States Patent
Böcking et al.

(10) Patent No.: US 8,722,437 B2
(45) Date of Patent: May 13, 2014

(54) METHOD OF COMPONENT ASSEMBLY ON A SUBSTRATE

(75) Inventors: Till Böcking, Boston, MA (US); John Justin Gooding, Chippendale (AU); Kristopher A. Kilian, Chicago, IL (US); Michael Gal, Engadine (AU); Katharina Gaus, Chippendale (AU); Peter John Reece, Abbotsford (AU); Qiao Hong, Westmead (AU)

(73) Assignee: Mogul Solutions LLC, Dover, DE (US)

( * ) Notice: Subject to any disclaimer, the term of this patent is extended or adjusted under 35 U.S.C. 154(b) by 842 days.

(21) Appl. No.: 12/740,734

(22) PCT Filed: Oct. 31, 2008

(86) PCT No.: PCT/AU2008/001616
§ 371 (c)(1),
(2), (4) Date: Jul. 26, 2010

(87) PCT Pub. No.: WO2009/055862
PCT Pub. Date: May 7, 2009

(65) Prior Publication Data
US 2010/0279394 A1    Nov. 4, 2010

Related U.S. Application Data

(63) Continuation-in-part of application No. 11/933,541, filed on Nov. 1, 2007.

(30) Foreign Application Priority Data

May 8, 2008   (AU) ................................ 2008902248

(51) Int. Cl.
*H01L 21/00*    (2006.01)
*H01L 21/98*    (2006.01)

(52) U.S. Cl.
USPC .................................. 438/29; 438/48; 438/49

(58) Field of Classification Search
USPC .................................................. 438/29, 48, 49
See application file for complete search history.

(56) References Cited

U.S. PATENT DOCUMENTS

| | | | |
|---|---|---|---|
| 6,652,808 B1 | 11/2003 | Heller et al. | |
| 6,974,604 B2 | 12/2005 | Hunter et al. | |
| 2003/0063748 A1 | 4/2003 | Shields | |
| 2004/0121520 A1 | 6/2004 | Karkkainen | |

FOREIGN PATENT DOCUMENTS

GB      2 366 666 A      3/2002

OTHER PUBLICATIONS http://www.healingtalks.com/tag/layers-of-aluminum-arsenide-with-the-gallium-arsenide/.
Chinese Office Action of counterpart Application No. 2008801197931, issued Jul. 27, 2011.

(Continued)

*Primary Examiner* — Evan Pert
(74) *Attorney, Agent, or Firm* — Baker & Hostetler LLP

(57) ABSTRACT

A method of component assembly on a substrate, and an assembly of a bound component on a substrate. The method comprises the steps of forming a free-standing component having an optical characteristic; providing a pattern of a first binding species on the substrate or the free standing component; and forming a bound component on the substrate through a binding interaction via the first binding species; wherein the bound component exhibits substantially the same optical characteristic compared to the free-standing component.

20 Claims, 21 Drawing Sheets

(56) References Cited

OTHER PUBLICATIONS

Cullis, A.G., et al., "The Structural and Luminescence Properties of Porous Silicon," J. Appl. Phys. 82 (3), Aug. 1997, pp. 909-965.

Stewart, M.P., et al., "Chemical and Biological Applications of Porous Silicon Technology," Advanced Materials, 12, 2000, pp. 859-869.

D'Auria, S., et al., "Nanostructured Silicon-based Biosensors for the Selective Identification of Analytes of Social Interest," J. Phys.: Condens. Matter 18, 2006, pp. S2019-S2028.

Marsh, G., "Porous Silicon a Useful Imperfection," Materials Today (Oxford United Kingdom), Jan. 5, 2002, pp. 36-41.

Islam, T., et al., "Study of Long-term Drift of a Porous Silicon Humidity Sensor and Its Compensation Using ANN Technique," Sens. Actuators, A FIELD Full Journal Title: Sensors and Actuators, A: Physical, 2007, A933, pp. 472-479.

Reece, P.J., et al., "Optical Properties of Erbium-Implanted Porous Silicon Microcavities," Applied Physics Letters, 85, 2004, pp. 3363-3365.

Rotiroti, L., et al., "Optical Microsensors for Pesticides Identification based on Porous Silicon Technology,"Biosensors & Bioelectronics, 20, 2005, pp. 2136-2139.

DeStefano, L., et al., "Resonant Cavity Enhanced Optical Microsensor for Molecular Interactions based on Porous Silicon," Physica Status Solidi (a) 203, No. 5, 2006, pp. 886-891.

DeLouise, L.A., et al., "Quantative Assessment of Enzyme Immobilization Capacity in Porous Silicon," Anal. Chem., 2004, 76, pp. 6915-6920.

DeLouise, L.A., et al., "Enzyme Immobilization in Porous Silicon: Quantitative Analysis of the Kinetic Parameters for Glutathione-S-Transferases," Analytical Chemistry, vol. 77, No. 7, Apr. 2005, pp. 1950-1956.

DeLouise, L.A., et al., "Cross-Correlation of Optical Microactivity Biosensor Response with Immobilized Enzyme Activity. Insights into Biosensor Sensitivity," Analytical Chemistry, vol. 77, No. 10, May 2005, pp. 3222-3230.

Ouyang, H., et al., "Macroporus Silicon Microcavities for Macromolecule Detection," Advanced Functional Materials, 2005, 15, pp. 1851-1859.

Ouyang, H. et al., "Label-Free Quantitative Detection of Protein Using Macroporous Silicon Photonic Bandga Biosensors," Analytical Chemistry, vol. 79, No. 4, Feb. 2007, pp. 1502-1506.

Ouyang, H., et al., "Quantitative Analysis of the Sensivity of Porous Silicon Optical Biosensors," Applied Physics Letters, 88, 2006, pp. 163108-1-163108-2.

Guo, L., et al., "Energy Transfer Between Collodial Semiconductor Nanocrystals in an Optical Microcavity," Applied Phystics Letters 89, 2006, pp. 061104-1-061104-3.

Lopez, H.A., et al., "Erbium Emission from Porous Silicon One-Dimensional Photonic Band Gap Structures," Applied Physics Letters, vol. 77, No. 23, Dec. 2000, pp. 3704-3706.

Koyama, H., et al., "Visible Photoluminescence of Porous Si and Its Related Optical Properties," Japanese Journal of Applied Physics, vol. 30, No. 12B, Dec. 1991, pp. 3606-3609.

Looyenga, H., et al., "Dielectric Constants of Heterogeneous Mixtures," Physica 31, 1965, pp. 401-406.

Squire, E.K., et al., "Light Emission from Porous Silicon Single and Multiple Cavities," Journal of Luminescence, 80, 1999, pp. 125-128.

Kilian, K.A., et al., "Si-C Linked Oligo(ethylene glycol) Layers in Silicon-based Photonic Crystals: Optimization for Implantable Optical Materials," Biomaterials, 28, 2007, pp. 3055-3062.

Kilian, K.A., et al., "Peptide-Modified Optical Filters for Detecting Protease Activity," ACS Nano, vol. 1, No. 4, 2007, pp. 355-361.

Kilian, K.A., et al., "Hybrid Lipid Bilayers in Nanostructured Silicon: a Biomimetic Mesoporous Scaffold for Optical Detection of Cholera Toxin," Chemical Communications, 2007, pp. 1936-1938.

Kilian, K.A., et al., "Forming Antifouling Organic Multilayers on Porous Silicon Rugate Filters Towards In Vivo/Ex Vivo Biophotonic Devices," Advanced Functional Materials, 2007, 17, pp. 2884-2890.

Kilian, K.A., et al., "Organic Modification of Mesoporous Silicon Rugate Filters: the Influence of Nanoarchitecture on Optical Behaviour," International Journal of Nanotechnology, vol. 5, Nos. 2/3, 2008, pp. 170-178.

Kilian, K.A., et al., "Introducing Distinctly Different Chemical Functionalities onto the Internal and External Surfaces of Mesoporous Materials," Angew. Chemi. Int., Ed., 2008, 47, pp. 2697-2699.

McNally, H., et al., "Self-Assembly of Micro- and Nano-scale Particles Using Bio-Inspired Events," Applied Surface Science, 214, 2003, pp. 109-119.

Onoe, H., et al., "Three-Dimensional Sequential Self-Assembly of Microscale Objects," Small, 2007, No. 8, pp. 1383-1389.

PCT/AU2008/001616 International Search Report, mailed Feb. 4, 2009.

METHOD OF COMPONENT ASSEMBLY ON A SUBSTRATE

CROSS-REFERENCE TO RELATED APPLICATION

This is a national stage application of PCT/AU2008/001616, filed Oct. 31, 2008, which is a continuation-in-part of U.S. application Ser. No. 11/933,541, filed Nov. 1, 2007, hereby incorporated by reference. This application also claims priority to Australian Application No. 2008902248, filed May 8, 2008, hereby incorporated by reference.

FIELD OF INVENTION

The present invention relates broadly to a method of component assembly on a substrate, to an assembly of a bound component on a substrate, to an sensor structure and a method of fabricating the same, and to a light emitting device and a method of fabricating the same.

BACKGROUND

The creation of integrated optical devices from separate micro-components has, in the past, required time-consuming and often manually intensive methods. Attempts to alleviate these difficulties have seen the emergence of more mechanized technologies that focus on assembly either via fluidic self-assembly or methods that are based on wafer-to-wafer transfer. Key to all these technologies is the substrate which is either a specifically prepared 'receptor' with precisely etched holes that are complementary to the optical components, or substrates that require equally stringent photolithographic alignment and/or masking. The current technologies used for the integration of optical components are restricted by the limited number of compatible substrates (e.g. silicon, silicon oxide, gallium arsenide).

Ideally, the optical designer should not be limited by the fabrication technology. For example, one should be able to integrate III-V light sources and detectors with Si based photonic crystals, modulators and/or micro-mirrors, with $SiO_2$ waveguides, and non-linear optical devices on any substrate. The function and/or complexity of an integrated optical circuit should not be restricted by the substrate.

"Strained layer epitaxy" is used to integrate semiconductors with dissimilar lattice structures, such as growing GaAs on Si, or SiGe alloys on Si, etc. However, this technique is only possible if the respective layer thicknesses are thinner than a critical thickness which is typically extremely thin. In addition, this technique is only useful for crystalline materials, and is not useful for integrating non-crystalline materials such as plastics and glasses. The use of MEMS (Micro-Electro-Mechanical Systems) for integrating mechanical components, sensors, etc with electronics on a silicon substrate using microelectronic technology is also made use of. This technology relies on devices, such as micro-mirrors, waveguides, cantilevers, etc that are Si (and $SiO_2$) based and are micromachined into Si. Again, this method is limited to Si and $SiO_2$ and is not useful to integrate other materials, such as GaAs, electro-optic materials, etc There are a number of other techniques that are grouped into 'top-down' and 'bottom-up' approaches. The top-down approach involves a block of material being processed into the desired shape and working unit. In bottom-up fabrication, small building blocks (usually nanoscale as the term originates from nanotechnology) are connected together to fabricate a functioning unit.

Current top-down approaches for integrating optical structures on a substrate typically involve fluidic assembly into defined 'holes' in a substrate, lithographic patterning followed by etching or wafer-to-wafer transfer. These are very complicated procedures that lack the ability to be easily scaled up and typically suffer from low fabrication success rates.

On the other hand, while there are many potential bottom-up strategies for fabricating optical structures on different materials, no current method for assembling high quality optical devices (prefabricated) on any substrate has been demonstrated. A sufficient understanding of how to assemble molecular building blocks with sufficient control to produce high quality materials (that is, comparable to microelectronics state of the art) has not been reached.

Recently, methods for electric field assisted self-assembly of functionalized DNA strands as building blocks for assembly and fabrication of devices have been proposed in U.S. Pat. No. 6,652,808. However, the methods disclosed in that document focus primarily on the control and chemical nature of the DNA based building blocks for bonding of components to a substrate, rather than providing any teaching with respect to the properties or functionality of the devices bound to the substrate. Furthermore, an approach for building a photonic band-gap structure is disclosed, where a photonic band-gap structure is built-up from metal beads exhibiting magnetic properties. The photonic band-gap structure is formed on the substrate through a process in which the metal beads are interconnected via DNA bonds. No optical characterization of such grown photonic band-gap structures is provided in that document.

Furthermore, there is no teaching provided in that document that verifies whether the alignment accuracy between the metal beads is actually sufficient to achieve a photonic crystal effect, and on which substrate or type of substrates. A technique for alignment of "larger" structures of the order of 10 to 100 microns is also discussed in that document, using selective derivatisation with different DNA sequences of a device to be positioned and oriented on a substrate. However, no teaching is provided with respect to handling of larger devices, thus limiting the proposed method to techniques in which the devices to be attached are smaller than about 100 microns, and with a need to apply individual devices in that size range to the substrate for assembly. The preparation of free-standing devices in that range of small sizes can constitute a major challenge in the overall assembly process, in particular with a view to mass-production of assemblies of devices on various substrates.

As an example application of integrated optical devices, currently, optical methods for sensing molecular species often require a sample cleanup, where the target analyte resides in a complex mixture of many different molecules. Many current optical methods also require the labeling of the analyte using for example, a fluorescent tag, and complex instrumentation that requires both transport of the sample to a laboratory and trained personnel. The prior art optical methods also require time-consuming protocols with long incubation periods, wash steps etc. The combination of these factors will often lead to the slow detection of a chemical or a biological molecule. However, in many situations, expediency is integral in detecting a substance for example, at times of environmental threat, point-of-care diagnosis, biological and chemical warfare. Hence, many prior art sensing technologies are inadequate. Although there are currently a number of label-free methods for sensing molecular species, these methods suffer from either non-specific detection issues, poor sensitivity compared to labeling approaches, incompatible formats for the field or other disadvantages such as complicated instrumentation, the need for skilled technicians or the need for sample cleanup or a combination of the above.

Photonic crystals formed by electrochemical etching porous silicon (PSi) are an example of 'hard' photonic crystals that can be fabricated by modulating the porosity and hence the refractive index of the layers during anodization [A. G. Cullis, L. T. Canham, P. D. J. Calcott, *Applied Physics Reviews* 1997, 82, 909.] The nanoporous architecture of the PSi material allows infiltration of gases and liquids within the material, thus modifying the average refractive index and the resultant spectral qualities. This quality of PSi materials has led to numerous investigations of PSi materials in optical sensing including gas, chemical and biological sensing. [M. P. Stewart, J. M. Buriak, *Adv. Mater.* (Weinheim, Ger.) FIELD Full Journal Title: Advanced Materials (Weinheim, Germany) 2000, 12, 859.; S. D'Auria, M. de Champdore, V. Aurilia, A. Parracino, M. Staiano, A. Vitale, M. Rossi, I. Rea, L. Rotiroti, A. M. Rossi, S. Borini, I. Rendina, L. De Stefano, *J. Phys.: Condens. Matter* FIELD Full Journal Title: Journal of Physics: Condensed Matter 2006, 18, S2019.; G. Marsh, *Mater. Today* (Oxford, U. K.) FIELD Full Journal Title: Materials Today (Oxford, United Kingdom) 2002, 5, 36.; T. Islam, H. Saha, *Sens. Actuators, A* FIELD Full Journal Title: Sensors and Actuators, A: Physical 2007, A133, 472.]

One type of PSi photonic crystal that has shown utility for sensing is the resonant microcavity. [P. J. Reece, M. Gal, H. H. Tan, C. Jagadish, *Applied Physics Letters* 2004, 85, 3363.; L. Rotiroti, L. D. Stefano, I. Rendina, L. Moretti, A. M. Rossi, A. Piccolo, *Biosensors & Bioelectronics* 2005, 20, 2136.; L. D. Stefano, I. Rea, I. Rendina, L. Rotiroti, M. Rossi, S. D'Auria, *Physica Status Solidi A: Applications and Materials Science* 2006, 203, 886.; L. A. DeLouise, B. L. Miller, *Analytical Chemistry* 2004, 76, 6915.; L. A. DeLouise, B. L. Miller, *Analytical Chemistry* 2005, 77, 1950.; L. A. DeLouise, P. M. Kou, B. L. Miller, *Analytical Chemistry* 2005, 77, 3222.; H. Ouyang, M. Christophersen, R. Viard, B. L. Miller, P. M. Fauchet, *Advanced Functional Materials* 2005, 15, 1851.; H. Ouyang, L. A. DeLouise, B. L. Miller, P. M. Fauchet, *Analytical Chemistry* 2007, 79, 1502.; H. Ouyang, C. C. Striemer, P. M. Fauchet, *Applied Physics Letters* 2006, 88, 163108.]. Microcavities are formed by incorporating a defect (spacer) layer within the periodicity of a multilayered 1-dimensional photonic crystal stack. Tuning the optical thickness (n·d, where n is the refractive index and d the thickness of the layer) of the spacer layer to $m\lambda/2$ ($\lambda$ is the central wavelength of the Bragg plateau, m is the spectral order) gives rise to a cavity resonance in the centre of the spectrum, where light of that wavelength "resonates" and therefore does not reflect.

In the prior arts using PSi microcavities for sensing stimuli such as biomolecules or chemicals etc., the infiltration of material can cause shifts in the entire spectrum that can be correlated to the influx of material throughout the nanoporous matrix. Another drawback to using microcavities for sensing in existing sensor designs associated with the requirement that stimuli must reach the central layer is that the stimuli will need to penetrate from the top layer of the micro cavity through the nanoporous architecture, a particular problem for large biomolecules (comparable to or larger than the smallest pore size in the alternating pore size multi layered stack pore size). Attempts to alleviate this problem have included enlarging the pore diameter which leads to decreased optical quality and sensitivity. [H. Ouyang, C. C. Striemer, P. M. Fauchet, *Applied Physics Letters* 2006, 88, 163108.] Other attempts to address this problem have included modifying the surface chemistry within the nanoporous matrix which may enhance the ingress of particular species, the diffusion issue is still not solved. Hence, the modification of surface chemistry may allow excellent control over the type of analyte captured but its use is still limited by the diffusion issue.

As another example application of integrated optical devices, currently, there is a research interest into fabricating Si integrated optical epitaxial light emitting structures for optoelectronic technologies. While II-VI quantum dot doped microcavities have been reported for $TiO_2$—$SiO_2$ distributed Bragg reflectors have been reported e.g. in [L Guo, T D Krauss, C B Poitras, M Lipson, X Teng and H Yang, *Applied Physics Letters* 89, 061104 (2006)], and ion doped porous Si microcavities e.g. in [H A Lopez and P M Fauchet, Applied Physics Letters 77, number 23, 4 Dec. 2000], the applicant is not aware of reports on quantum dot doped microcavities formed using Si integrated optical epitaxial techniques.

The present invention has been made in view of the above described background to seek to address one or more of the above-mentioned problems.

SUMMARY

In accordance with a first aspect of the present invention there is provided a method of component assembly on a substrate, the method comprising the steps of forming a free-standing component having an optical characteristic; providing a pattern of a first binding species on the substrate or the free standing component; and forming a bound component on the substrate through a binding interaction via the first binding species; wherein the bound component exhibits substantially the same optical characteristic compared to the free-standing component.

In accordance with a second aspect of the present invention there is provided a assembly comprising a substrate; and a bound component assembled on the substrate through a binding interaction via a first binding species provided on the substrate or on a free-standing pre-form of the bound component; wherein the bound component exhibits substantially a same optical characteristic compared to the free-standing pre-form.

In accordance with a third aspect of the present invention there is provided a sensor structure comprising a first Bragg mirror; a second Bragg mirror; and a stimuli responsive material disposed between the first and second Bragg mirrors; wherein the second Bragg mirror is assembled on the first Bragg mirror by a binding interaction via the stimuli responsive material.

In accordance with a fourth aspect of the present invention there is provided a method for fabricating a sensor structure, the method comprising the steps of providing a first Bragg mirror; providing a second Bragg mirror; and providing a stimuli responsive material disposed between the first and second Bragg mirrors; wherein the second Bragg mirror is assembled on the first Bragg mirror by a binding interaction via the stimuli responsive material.

In accordance with a fifth aspect of the present invention there is provided a method of fabricating a light emitting device, the method comprising the steps of providing a first Bragg mirror; providing a second Bragg mirror; and providing a light emitting material disposed at an interface between the first and second Bragg mirrors; wherein the second Bragg mirror is assembled on the first Bragg mirror by a binding interaction via the light emitting material.

In accordance with a sixth aspect of the present invention there is provided a light emitting device comprising a first Bragg mirror; a second Bragg mirror; and a light emitting material disposed at an interface between the first and second Bragg mirrors; wherein the second Bragg mirror is assembled on the first Bragg mirror by a binding interaction via the light emitting material.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
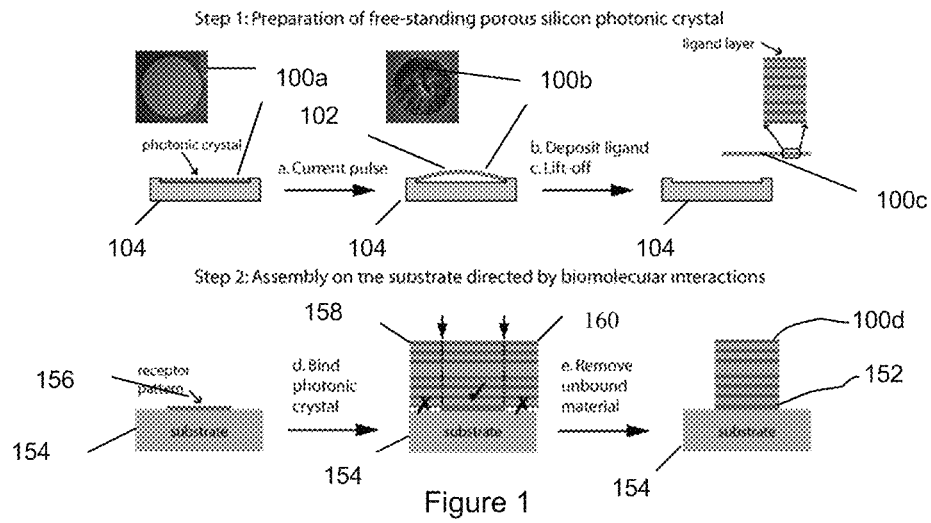
FIG. 1 shows a schematic representation of assembly of optical components according to an example embodiment.
Figure 2:
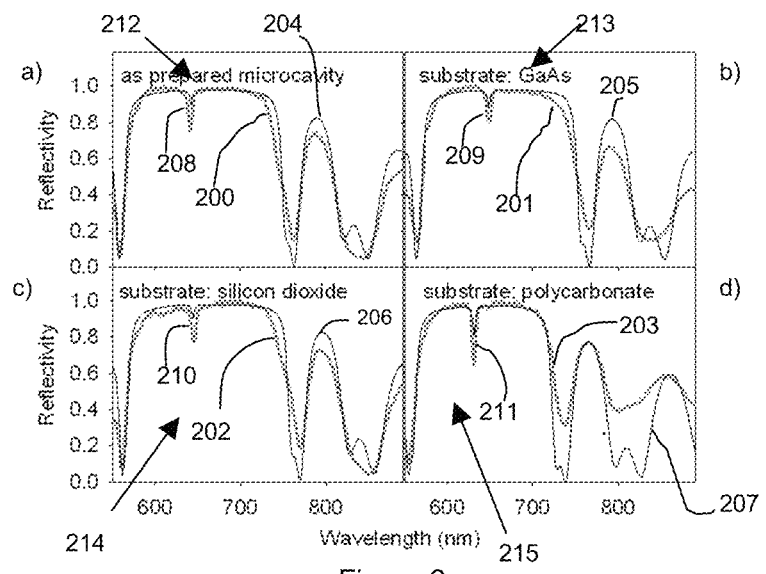
FIGS. 2a to d show the characteristic optical reflectivity spectra of a PSi microcavity as prepared, and assembled on GaAs, silicon dioxide and poly carbonate respectively, using the method of FIG. 1.

The integration of different optical components on the same substrate, as well as optical components with electronic devices, has been hindered by different components typically being made of different materials. Hence a problem has existed where either optical components are all made from the same material, hence compromising the performance of some or all of the components, or the problem has been how to integrate components made from the different materials onto the same substrate. Thus the problem is one of material incompatibility. The described example embodiments provide methods that can overcome this problem by harnessing the recognition properties of biological molecules to enable the assembly of optical materials on any substrate. Porous silicon (PSi) microcavities and Bragg mirrors are fabricated and assembled on silicon, gallium arsenide and plastic. The substrate material is modified by application of a biological molecule to define the location for assembly. Optical components modified with the complementary biomolecule self-assemble only onto the correct location without compromising their optical integrity. In another embodiment optical components can be deposited onto and adhered to a substrate via patterns of an adhesive ultrathin coating. Furthermore, the technique in the example embodiments allows assembly of new devices from components of different composition as demonstrated by incorporating different spacer layers between porous silicon Bragg mirrors to create a resonant microcavity.

Described embodiments use biomolecule directed or adhesive coating directed assembly of prefabricated high quality optical structures on the micro and macroscale without micromachining requirements. In contrast to biomolecule directed assembly of photonic crystals from colloidal building blocks (described e.g. in U.S. Pat. No. 6,752,868 B2), which cannot produce the high quality optical structures required for the fabrication of optical circuits, in example embodiments high quality Bragg mirrors and resonant microcavities were formed by anodization of silicon. In one embodiment, the macroscale assembly of optical films occurs on substrates patterned with complementary biological molecules. The high affinity of biorecognition causes assembly at the applied pattern only, while the remainder of the film fractures upon rinsing and drying steps leaving a macroscale pattern of optical structures (>1 mm). In another embodiment, a macroscopic free-standing optical structure was fractured by sonication in ethanol to produce microparticles (<100 μm). Utilizing biorecognition, the optical microparticles are assembled in the correct orientation when applied to the biomolecule labelled substrate. Example embodiments of the present invention can create optically flat materials on a macroscale such that high quality optical characteristics are maintained. In contrast to building an optical structure using the bottom up approach, example embodiments can allow assembly of prefabricated high quality optical components over multiple length scales.

Example embodiments assemble optical materials on any substrate that allows biorecognition or deposition of thin coatings to mate the materials together. In one embodiment, resonant microcavities fabricated with porous silicon were removed from silicon and coated with biorecognition molecules. A number of substrates including: silicon, silicon dioxide, galium arsenide and polycarbonate, were patterned with aqueous solutions of complementary biomolecules. Application of the labelled microcavities to the patterned substrates yielded assembly at the biomolecular pattern only, while the remaining microcavity was rinsed away with ethanol.

Example embodiments provide a combination of high quality top-down optical structure fabrication techniques with a bottom-up assembly method (a hybrid approach) exploiting biorecognition or an adhesive coating to form new devices. Previous work on assembling optical structures has involved either 1) the top-down fabrication of optical materials (e.g. PSi microcavity formation) or 2) bottom-up assembly of new optical materials (e.g. colloidal crystal fabrication). By first forming high quality optical materials using top-down fabrication followed by e.g. biomolecule directed assembly of multiple components, a high quality optical structure can be created in example embodiments. Other materials (e.g. responsive polymers and small molecules, metals, nanoparticles and objects, redox and photosynthetic proteins, molecular wires, carbon nanotubes, ionic liquids/liquid crystals, lipid layers, cells, diatoms, silica and polymer beads and many other functional molecules and materials) can be incorporated with the high quality optical structures such that novel properties and new emergent functions may be harnessed.

FIG. 1 shows a schematic representation of the assembly of optical components by specific adhesion onto any substrate via biomolecular interactions in an example embodiment.

Porous Silicon (Psi) optical resonant microcavities (1D photonic crystals) are prepared as free-standing films 100c in a first sequence and then deposited via biorecognition-mediated self-assembly onto a substrate 154 in a second sequence. The photographs in FIG. 1 show top views of an as prepared PSi Bragg mirror 100a and the PSi Bragg mirror 100b after application of a current pulse. The PSi film 100b remains attached to the wafer 104 around the edge allowing modification with proteins on the top surface 102 while the bottom surface remains unmodified. It is noted that the components are not drawn to scale; the thickness of the free-standing PSi photonic crystal 100c is between 1.5-3 μm whereas the thickness of the combined ligand and receptor layer 152 is in the order of 10 nm. The assembly of microcavities with spacer layers of optical thickness corresponding to the half wavelength of visible light ($n \cdot d = \lambda/2$) in the example embodiment demonstrates the capability to assemble delicate optical devices that can be tested and characterized. PSi has proven to be particularly well-suited for the production of high quality optical devices, such as one-dimensional photonic crystals including Bragg mirrors, optical filters and microcavities, as its refractive index can be precisely and continuously tuned between approximately 1.3 and 3.0. The PSi based microcavities are fabricated by electrochemical etching the single crystal Si wafer 104, whereby the etching-current density determines the porosity and hence the refractive index of the material.

For the PSi film 100a photonic crystal formation, the Si(100) wafer 104 (p++, B-doped, 0.005 Ωohm cm, single side polished) was cleaned by sonication in ethanol and acetone and blown dry under a stream of nitrogen. The cleaned wafer 104 was etched in an electrochemical cell with a polished stainless steel electrode as back-contact and a Pt ring counter electrode using 25% ethanolic HF (mixture of 50% aqueous HF and 100% ethanol, 1:1, v/v) as electrolyte. The power supply was controlled using custom written software to modulate the current density and etching times during the etching process. Etch stops were incorporated into the etching program to allow recovery of the HF concentration at the etching front. The current densities and etch times required to obtain the PSi layer 100a of desired porosity and thickness were calculated from calibration curves obtained for each batch of Si wafers and etching solutions.

At the end of the electrochemical etching that creates the cavity, a high current pulse is applied (FIG. 1, Step a) to lift-off most of the microcavity from the underlying Si wafer 104. As a result, the approximately 3 μm thick PSi film 100b (microcavity), in this example, becomes free from the underlying substrate but remains attached at the edges. Maintaining the cavity attached to the Si wafer 104 is advantageous to enable simple further modifications for the self-assembly process. For details of a suitable technique to achieve "lift-off" reference is made to [H. Koyama, M. Araki, Y. Yamamoto, N. Koshida, *Japanese Journal of Applied Physics* 30, 3606 (1991)], the contents of which are hereby incorporated by cross reference. After lift-off, the sample was carefully rinsed with ethanol followed by pentane and dried under a very gentle stream of nitrogen with gentle heating. The modification employed in this example involves the physisorption of a particular biorecognition element (e.g. a ligand) onto the exposed surface 102 of the microcavity 100b (FIG. 1, Step b). Proteins (e.g. avidin or biotinylated albumin) were deposited onto the hydrophobic surface of as-prepared PSi film 100b by physisorption from aqueous solution. Aqueous solutions do not enter the pores of as-prepared PSi film 100b.

Subsequently, the modified device 100c is released from the Si wafer 104 (FIG. 1, Step c) and inverted onto a substrate 154 of choice which is pre-modified with a pattern of the complementary biomolecular species 156 (e.g. a receptor) (FIG. 1, Step d). The protein-modified lift-off sample 100b (still attached at its edge to the underlying Si wafer 104) was released from the Si wafer 104 by scoring the edge of the PSi film 100b with a sharp tip and floating the released PSi film 100c off the Si wafer 104 in this example embodiment. The assembly substrate 154 was spotted with solutions of protein to define the positions for adhesion. Subsequently, poly(ethylene glycol) was physisorbed elsewhere onto the substrate surface as a blocking species in this example embodiment to diminish binding of the protein-modified free-standing Psi film 100c to the bare substrate 154 surface. Portions 158, 160 of the PSi photonic crystal 100c not bound to the substrate 154 via the biorecognition pair 152 can simply be washed away to leave microcavities 100d only bound at positions determined by the receptor pattern 156 on the substrate 154 (FIG. 1, Step e). The substrate 154 was then vigorously rinsed to remove non-bound or weakly bound portions 158, 160 of the PSi film 100c elsewhere on the substrate 154. Removal of avidin-modified portions 158, 160 non-specifically adhering to the BSA-coated substrate 154 areas was performed using a detergent in the removal process in the example embodiment. Depending on the nature of the binding species in different embodiments, the use of a detergent is optional.

It is noted that other blocking species may be used in different embodiment, including, but not limited to, thin films of or self assembled monolayers (SAMs) terminated with
- ethers and derivatives of poly-/oligo-(ethylene glycol)
- amines/ammonium salts
- amides, amino acids, peptides
- Crown ethers
- sugars, polyols (eg mannitol)
- surfactants (eg Triton X-100)
- zwitterionic groups (eg phosphrylcholine)
- perfluorinated groups
- protein
- synthetic polymers
- natural polymers or combinations thereof. It is noted that, depending on the nature of the binding species in different embodiments, the use of a blocking species is optional.

As seen in FIG. 1, the method in the example embodiment results in an assembly comprising the substrate 154 and the bound microcavities 100d assembled on the substrate 154 through a binding interaction via a binding species in the form of a biorecognition pair. In another embodiment described below, the binding species can be in the form of an adhesive layer provided on the substrate or the free-standing component.

It is important to note that the optical properties of the devices advantageously remain the same independent of the substrate in different example embodiments. FIGS. 2a-d show the characteristic optical reflectivity spectra 200 to 203 of the same PSi microcavity (compare 100d in FIG. 1) as prepared (before lift-off), and assembled on GaAs, silicon dioxide and polycarbonate, respectively, as directed by the interaction between the protein avidin on the device and spots of the complementary biotinylated bovine serum albumin (BSA) on the substrate. Lines 204-207 represent simulations of the structures. The parameters used for the simulations are given in Table 1 below. The simulations are based on the effective medium formula by Looyenga (Physica 31, 401-406, 1965), which has been validated for p++-type PSi (Squire et al, J Lumin 80, 125-128, 1999):

$$n_{PSi}^{1/3} = (1-p)n_{Si}^{1/3} + pn_{air}^{1/3}$$

The starting parameters of the simulation (layer thickness and porosity) were taken from the etching program which calculates current density and etch times for a desired layer thickness and porosity from calibration curves. The values were then refined to achieve good agreement between the measured spectrum and the simulation. For a number of samples the total thickness of the PSi sample was determined by profilometry to validate the layer thickness values used in the simulations. In FIG. 2a-d, L=low porosity (high refractive index) layer, H=high porosity (low refractive index) layer, S=spacer layer, d=layer thickness, n=refractive index. The structure of the microcavities is $(LH)_7L$-$S$-$(LH)_9L$.

TABLE 1

| layer | d/nm | n |
|---|---|---|
| as prepared | | |
| L | 62 | 2.24 |
| H | 91 | 1.60 |
| S | 186 | 1.60 |
| GaAs | | |
| L | 62 | 2.25 |
| H | 91 | 1.62 |
| S | 187 | 1.62 |
| silicon dioxide | | |
| L | 62 | 2.26 |
| H | 91 | 1.61 |
| S | 184 | 1.61 |
| polycarbonate | | |
| L | 62 | 2.13 |
| H | 91 | 1.62 |
| S | 182 | 1.62 |

The reflection spectra 200-203 of the optical cavity are characterized by sharp 'dips' 208-211 in the reflectivity at the resonant frequency in the Bragg plateaus 212-215 (the regions of high reflectivity). The position and spectral width of the resonance is a sensitive measure of the structure and quality of the cavity. As can be seen in FIG. 2a-d, the cavity resonance is at approximately the same frequency (wavelength) and has approximately the same width for all substrate types, indicating that the cavity is impervious to the substrate.

Figure 3:
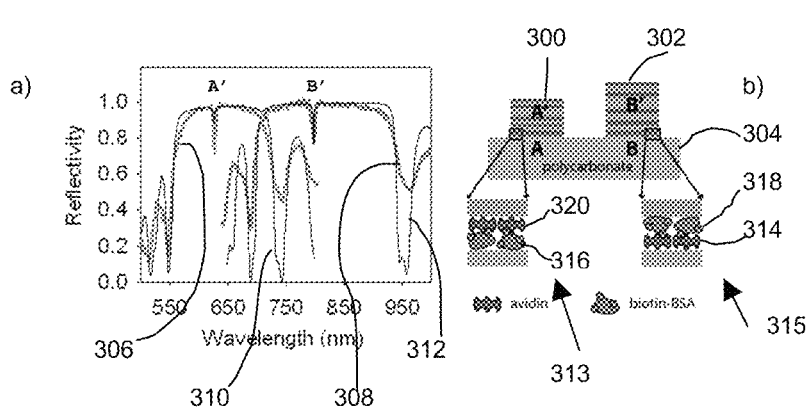
FIG. 3a shows reflectivity spectra of two different microcavities assembled on the same polycarbonate substrate using the method of FIG. 3b.
FIG. 3b shows a schematic representation of attachment of two different microcavities onto different locations of the same substrate according to an example embodiment.

As a self-assembly approach, an advantage of the described embodiments is the possibility of depositing several components simultaneously without the need to individually align them at the desired locations on the substrate, as this task is performed by the biorecognition. Another benefit of using biorecognition to assemble optical structures in the example embodiments is the possibility to self-assemble different optical components onto the same substrate by using different biorecognition pairs. This concept is demonstrated in FIG. 3b showing the attachment of two different microcavities 300, 302 with distinct resonant frequencies, onto different locations of the same substrate 304 which, in this example embodiment, is a polycarbonate film. The measured reflectivity spectra 306, 308 of the two different microcavities 300, 302 assembled on the same polycarbonate substrate 304 as directed by biomolecular interactions are shown in FIG. 3a. Lines 310, 312 represent simulations of the structures. FIG. 3b also schematically shows the biorecognition pairs 313, 315 for the respective structures 300, 302 deposited at defined positions on the substrate 304.

In this example, at location B the substrate 304 is modified with avidin 314, whilst at location A the substrate 304 is modified with biotinylated BSA 316. The two separate free standing microcavities, B' 300 and A' 302, are modified with biotinylated BSA 318 and avidin 320, respectively. Biorecognition therefore dictates that cavity A' 300 assembles at position A, and similarly, the avidin modified cavity B' 302 binds to the biotinylated substrate 304 at location B. It was found that cavity B' 302 did not assemble over spot A or vice versa. Also, there is no need to align each optical cavity 300, 302 precisely with its respective receptor spot(s) 314, 316 on the substrate 304. Unbound regions of the deposited free-standing structure simply break away during the washing step (compare FIG. 1, Step e).

Figure 4:
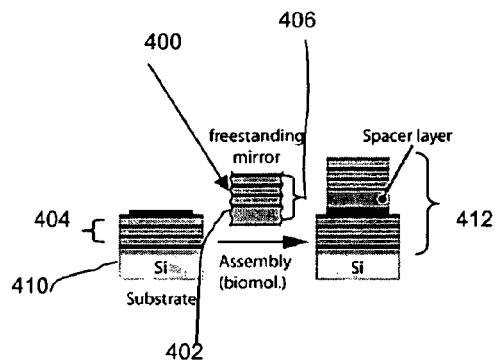
FIG. 4 shows a schematic representation of the assembly of microcavities from parts according to an example embodiment.

In other embodiments, biorecognition is also capable of self-assembling optical devices from separate components. In one example, PSi microcavities were assembled from two independent Bragg mirrors using biorecognition to create the desired resonant cavities. The steps used are shown in FIG. 4, which shows a schematic representation of the assembly of microcavities from parts in one example embodiment. A free-standing Bragg mirror 400 with spacer layer 402 is bound to a substrate Bragg mirror 404 via biomolecular interactions. The free standing PSI film 406 consisting of the Bragg mirror 400 and the spacer layer 402 is placed onto the PSI Bragg mirror 404 that was grown on a substrate 410. Biorecognition is used to mate the two parts to form the cavity 412. The assembly of microcavities was chosen to demonstrate the robustness and integrity of the biomolecular self-assembly approach as any non-uniformity in the produced spacer layer microcavity will result in poor optical characteristics.

Figure 5:
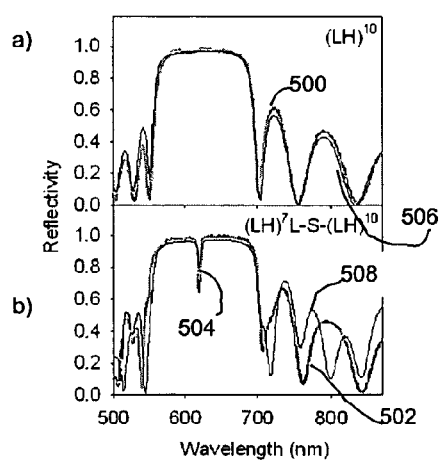
FIGS. 5a and b show reflectivity spectra of structures fabricated using the method of FIG. 4 before and after assembly of mirrors.

To test the formation of a cavity resonance, the reflectivity spectra 500, 502 of the structures were measured before and after assembly of the mirrors, shown in FIGS. 5a and b respectively. Prior to assembly of the free-standing mirror, the Bragg plateau of the substrate mirror spans a wavelength range of 550 to 700 nm. The successful assembly of the microcavity on the substrate is confirmed by the appearance of the pronounced cavity resonance 504 at 620 nm. As the cavity resonance is particularly sensitive to the parallelism of the two mirrors and the homogeneity of the spacer layer, it can be concluded that self-assembly based on biorecognition in this example embodiment is compatible with optical manufacturing of subtle devices. The deposited Bragg mirror consists of seven periods of alternating low and high porosity layers followed by a high porosity spacer layer. Lines 506, 508 represent simulations of the reflectivity. L=low porosity (high refractive index) layer, H=high porosity (low refractive index) layer, S=spacer layer. The parameters used for the simulations are given in Table 2.

TABLE 2

| Layer | d (nm) | n |
|---|---|---|
| Bragg mirror | | |
| L | 62 | 2.08 |
| H | 91 | 1.63 |
| Microcavity | | |
| L | 62 | 2.08 |
| H | 91 | 1.60 |
| S | 184 | 1.60 |

Figure 6:
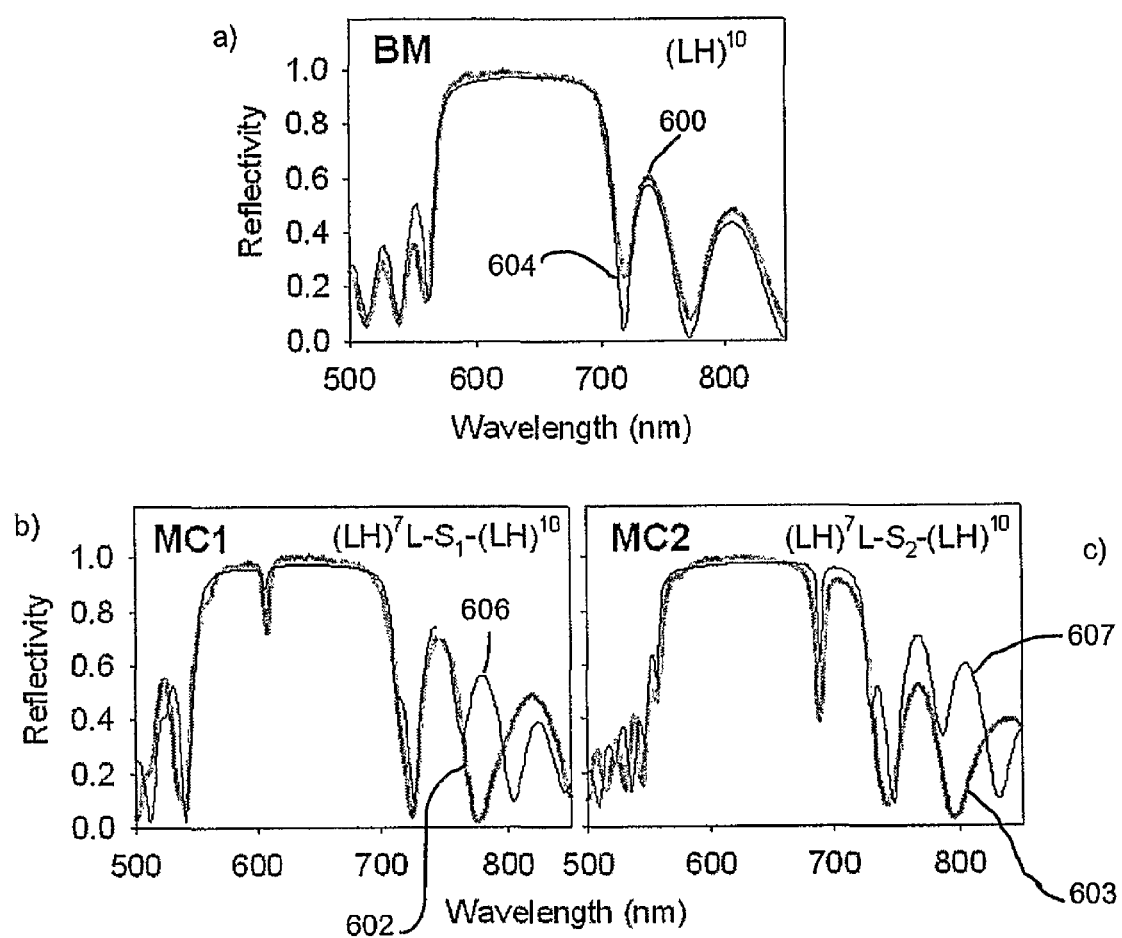
FIGS. 6a to c show reflectivity spectra of a Bragg mirror and different assembled microcavity structures fabricated using the method of FIG. 4.

To further test this capability, several cavities with spacer layers of different optical thicknesses (which can be achieved either by varying the thickness or the porosity of the layer) were fabricated via deposition of a Bragg mirror with integral spacer layer, and the cavity resonance was always in agreement with theoretical predictions. FIGS. 6a to c show reflectivity spectra 600, 602, and 603 of a substrate Bragg mirror (BM) and different assembled microcavity structures respectively, assembled on the same substrate as directed by biomolecular interactions using the approach described above with reference to FIG. 4. Lines 604, 606, and 607 represent simulations of the structures. The parameters used for the simulations are given in Table 3. In FIG. 6, L=low porosity (high refractive index) layer, H=high porosity (low refractive index) layer, S=spacer layer.

TABLE 3

| layer | d/nm | n |
|---|---|---|
| Bragg mirror (BM) | | |
| L | 62 | 2.15 |
| H | 89 | 1.63 |
| microcavity (MC1) | | |
| L | 62 | 2.15 |
| H | 89 | 1.58 |
| S | 169 | 1.58 |
| microcavity (MC2) | | |
| L | 62 | 2.20 |
| H | 89 | 1.57 |
| S | 256 | 1.57 |

Figure 7:
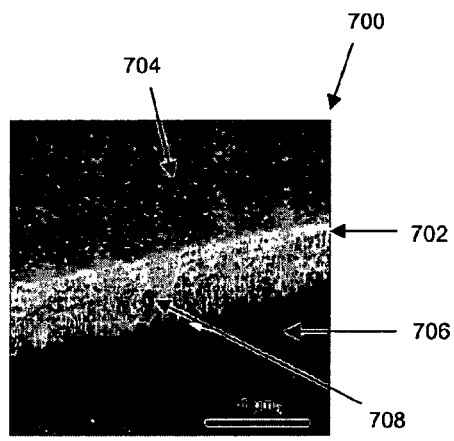
FIG. 7 shows a scanning electron microscopy (SEM) image of a structure fabricated using the method of FIG. 4.
Figure 8:
FIG. 8 shows a profilometry trace of the structure of FIG. 7.

Further evidence for the uniformity of the assembly of optical structures is obtained from SEM and profilometry measurements. The SEM image 700 in FIG. 7 shows the edge 702 of a 1.5 μm thick PSi Bragg mirror film 704 bound to a substrate mirror 706 via biorecognition. The spacer layer of the microcavity (etched as an integral part of the free-standing mirror) is apparent as a distinct layer 708 adjacent to the substrate 706. The uniformity of the binding between the two components over a large length scale is also apparent in the profilometry trace 800 shown in FIG. 8. The adhesion resulting from the multiple biomolecular interactions between the two optical components was sufficiently robust that the structures remained intact even after prolonged sonication in water or ethanol.

Figure 9:
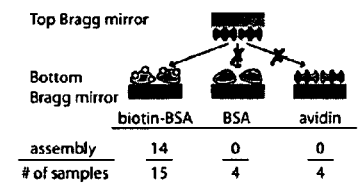
FIG. 9 shows details of the success rate of assembling a final microcavity using the method of FIG. 4.

Apart from being able to assemble or form high quality optical structures, the usefulness of the biomolecular self-assembly technique in the example embodiments is determined by the success rate of forming the correct device in the correct location. FIG. 9 provides details of the success rate of assembling the final microcavity. When the substrate reflector was modified with biotinylated BSA, 14 out of 15 avidin-modified lift-off reflectors correctly assembled into the specific microcavity. Significantly, when the substrate reflector was modified with either BSA alone (i.e. no conjugated biotin) or avidin, then no microcavities were successfully assembled. Hence the specific biological binding reaction is the condition for device assembly in such embodiments.

Figure 10:
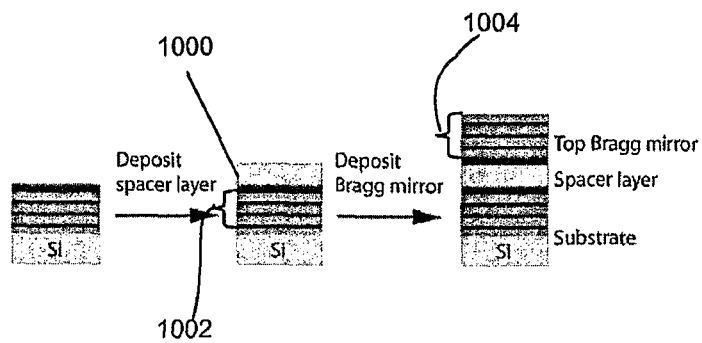
FIG. 10 is a schematic representation showing assembly of microcavities on a substrate using a sandwich approach according to another embodiment.
Figure 11:
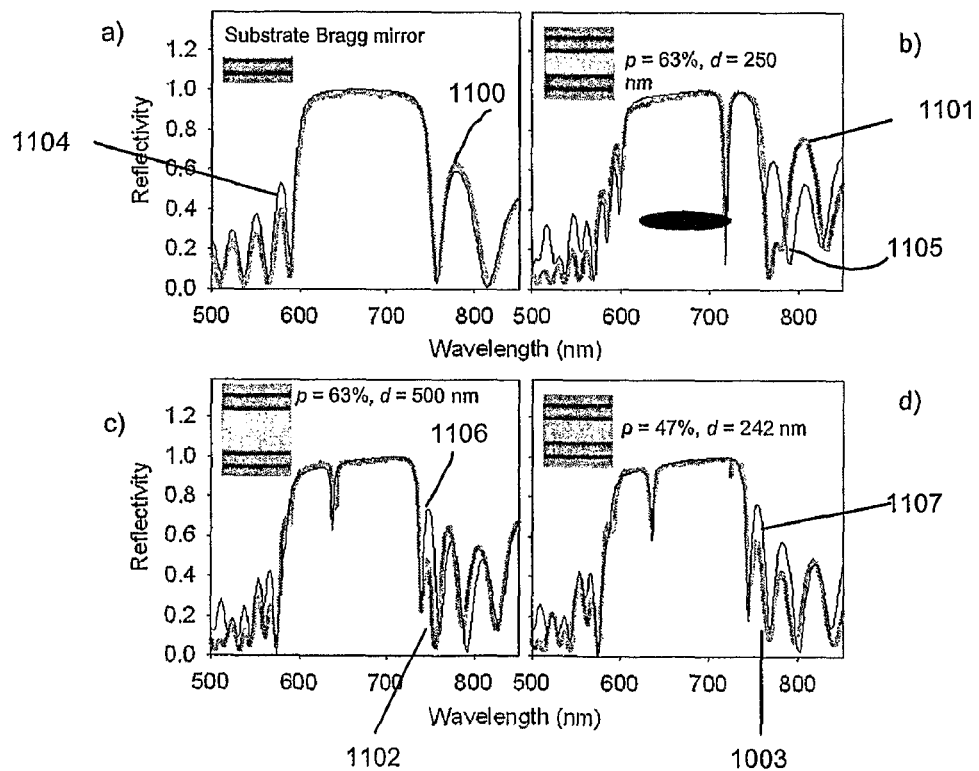
FIGS. 11a to d show the optical properties of a substrate reflector and formed microcavities with different spacer layers respectively fabricated using the method of FIG. 10.

Using separate components to assemble optical structures has additional benefits. In the case of optical microcavities, the method of example embodiments can allow complete flexibility in choosing the mirrors and the spacer layer. FIG. 10 shows assembly of microcavities on Si using a sandwich approach: First a spacer layer 1000 is deposited onto a substrate Bragg mirror 1002, in this example embodiment using assembly of a free standing spacer layer 1000 via bio recognition or an adhesive coating, followed by assembling the top Bragg mirror 1004 on the spacer layer 1000 via bio recognition or an adhesive coating. For example, this technique would make it possible to build vertical cavity surface emitting lasers (VCSELs) using PSi mirrors and III-V spacer layers, or III-V mirrors and Er:glass spacer layer, or insert a sensitized spacer layer into a cavity. FIGS. 11a-d show the optical properties of the substrate reflector and the formed microcavities where different spacer layers, grown as separate PSi thin films with different porosities and thicknesses, were embedded into the cavity Adhesion was achieved using proteins deposited onto the PSi spacer layer. FIG. 11a shows the spectrum 1100 of the underlying (substrate) Bragg mirror consisting of ten periods of alternating high and low refractive index layers. FIGS. 10b-d show the spectra 1101-1103 of sandwich structures with different porosity (refractive index) or thickness spacer layers as indicated. The free-standing Bragg mirror deposited onto the spacer layer to complete the microcavity structure consists of 8 periods of alternating low and high refractive index layers. Lines 1104-1107 show simulations of the optical structures. The parameters used for the simulations are given in Table 4.

TABLE 4

| | | layer | d/nm | n |
|---|---|---|---|---|
| a) | | | | |
| | Bragg mirror (10 periods) | L | 68 | 2.15 |
| | | H | 92 | 1.62 |
| b) | | | | |
| | (8 periods) | L | 65 | 2.15 |
| | | H | 95 | 1.64 |
| | spacer layer (p = 63%) | S1 | 250 | 1.69 |
| | Bragg mirror (10 periods) | | | |
| c) | | | | |
| | (8 periods) | L | 67 | 2.15 |
| | | H | 91 | 1.62 |
| | spacer layer (p = 63%) | S2 | 500 | 1.69 |
| | Bragg mirror (10 periods) | | | |
| d) | | | | |
| | (8 periods) | L | 68 | 2.16 |
| | | H | 91 | 1.62 |
| | spacer layer (p = 47%) | S3 | 242 | 2.06 |
| | Bragg mirror (10 periods) | | | |

In a further embodiment, poly(methyl methacrylate) (PMMA), a common laser gain medium and lithographic material, was spin-coated onto a substrate mirror followed by assembling a free-standing mirror to define the microcavity. It was found that by spin-coating different thickness polymer layers, the frequency (wavelength) of the final cavity resonance can be easily tuned. This embodiment enables the integration of organic materials with (inorganic) high quality optical components.

Figure 12:
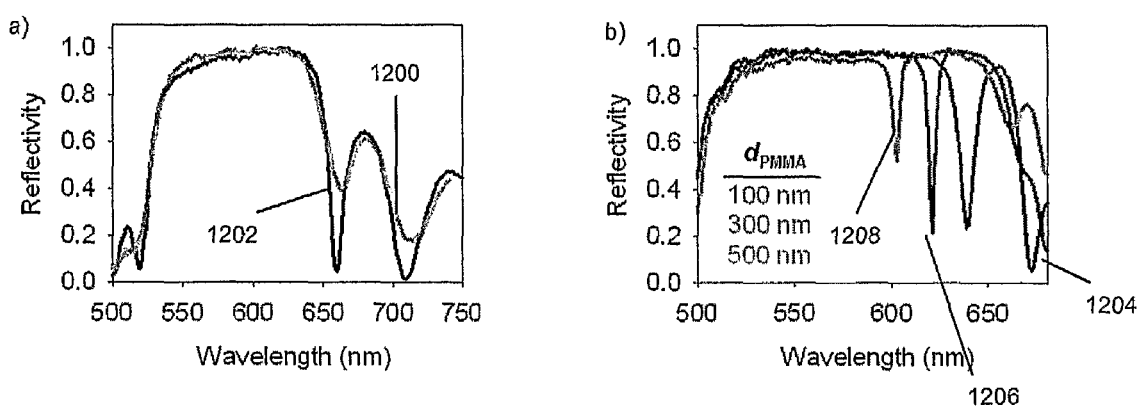
FIG. 12a shows reflectivity spectra of a PSi Bragg mirror before and after deposition of a PMMA layer by spin coating, according to another example embodiment.
FIG. 12b shows reflectivity spectra of microcavities fabricated using a PMMA spacer layer in the method of FIG. 10.

FIG. 12a shows reflectivity spectra 1200, 1202 of a PSi Bragg mirror before and after deposition of an approximately 500 nm thick layer of PMMA by spin coating respectively. The positions of the Bragg plateau and the interference fringes do not shift after deposition of PMMA, which demonstrates that the polymer did not enter the pores of the PSi structure, i.e. the properties of the cavity layer can be adjusted without altering the composition and optical properties of the Bragg mirror. FIG. 12b shows reflectivity spectra 1204, 1206, and 1208 of microcavities fabricated by the approach described above with reference to FIG. 10 with a PMMA polymer spacer layer (deposited by spin coating) of thicknesses of 100 nm, 300 nm, and 500 nm respectively. The thickness was determined by the manufacturer spin coating PMMA protocol in the example embodiments.

Figure 13:
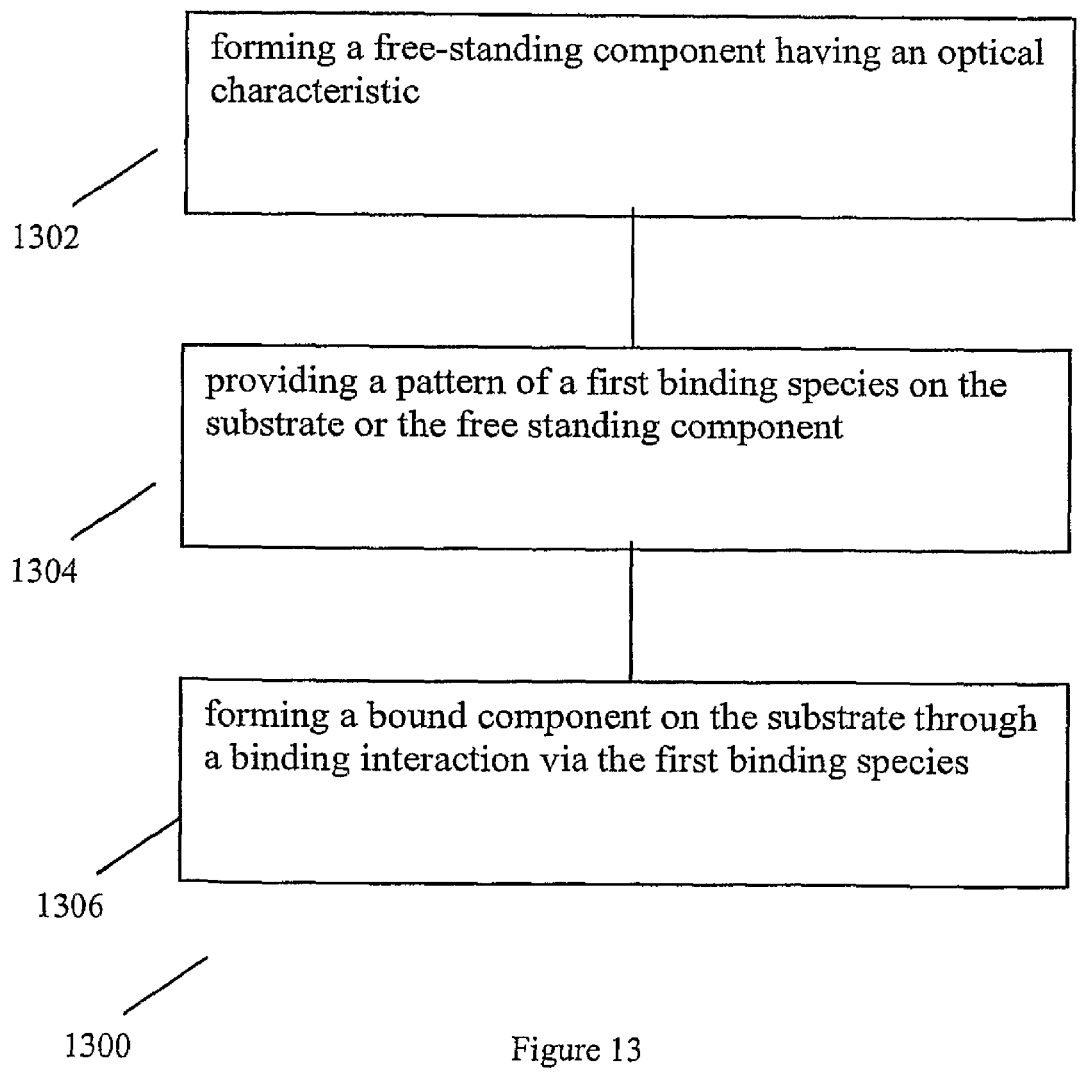
FIG. 13 shows a flow chart illustrating a method of component assembly on a substrate according to an example embodiment.

FIG. 13 shows a flow chart 1300 illustrating a method of component assembly on a substrate according to an example embodiment. At step 1302, a free-standing component having an optical characteristic is formed. At step 1304, a pattern of a first binding species is provided on the substrate or the free standing component. At step 1306, a bound component is formed on the substrate through a binding interaction via the first binding species, wherein the bound component exhibits substantially the same optical characteristic compared to the free-standing component.

The high degree of strength and uniformity imparted with biorecognition or with the use of adhesive coatings and the prospect of removing unbound material makes the approach in the example embodiments amenable to lithographic patterning. For instance, inkjet printing or soft lithographic stamping of proteins could define the circuit geography and deposition of silicon photonic material accomplished by the methods of the example embodiments. Furthermore, the approach can be extended for any optical material such that patterning different biomolecules for mixing different components could provide unprecedented ease and flexibility in optoelectronic circuit construction especially when taking into account the wide range of surface functionality that can be introduced on semiconductors (e.g. via hydrosilylation chemistry for Si and PSi), metals and polymers. Incorporating the cavity layer separately was demonstrated using thin PSi layers and PMMA in example embodiments. Different doping schemes can allow material to be confined exclusively to the cavity layer, a major advantage to using PSi for lasing applications. Incorporating alternative polymeric materials into the resultant photonic assembly is also possible and can open the door for new composite materials for diverse applications (e.g. laser gain medium, optical switches, biosensing at the cavity layer etc.).

The described embodiments provide methods that utilize biological recognition as a driving force for assembling photonic components into more complex architectures on a larger range of substrates. With the continued need to develop robust and flexible strategies to incorporate photonic components into complex devices, this advance expands current capabilities into composite materials. In conjunction with the evolving landscape of lithographic techniques and nanofabrication, harnessing the power of nature's complexity with self-assembling systems in the example embodiments can become a powerful synergistic tool for technological advancement in e.g. the photonic industries.

Current strategies for integrating optical components on a substrate require wafer-to-wafer transfer or photolithographic masking and etching to define a precise pattern that physically holds the optical components. In contrast, in the described embodiments, registration of optical components can be performed by spotting a biomolecule solution in a defined location. Importantly, the biomolecule pattern on the substrate dictates the patterning such that rinsing removes any non-specifically bound optical material. Thus the example embodiments allow a simple and flexible method to spatially array optical components which is amenable to existing liquid handling techniques, such as inkjet printing or soft lithographic stamping.

The described embodiments can provide a platform technology that allows, inter alia, Integration of any optical material with any substrate thus eliminating issues of compatibility between the different materials that are better suited for each type of optical component.

Simple application of a biological species in a defined pattern dictating the geography for assembling the component thus providing a simple method of patterning and registration.

By integrating different components on any substrate and simplifying the registration of optical components on the substrate, the example embodiments can lead to new and novel materials and even multiple different materials to be incorporated into optical devices by using the described biological assembly approach. This described methods in example embodiments have the potential to revolutionize the way optical devices and integrated optical circuits are fabricated and thus can lead to improvements in current technologies and many novel devices.

The example embodiments can allow virtually unlimited resources for fabrication diversity. For instance, different combinations of the four bases of DNA or RNA for hybridization assembly, using DNA ligands that bind proteins, called aptamers, can be fabricated and screened using a process called SELEX, monoclonal/polyclonal antibody production for many different antigens, phage display library screening to optimize recognition, use of combinatorial peptide libraries for the selection of peptides binding to inorganic substrates, protein:protein recognition. Thus the choice of assembly pairs can be very large including interactions such as van der Waals forces, hydrogen bonding, hydrophobic/hydrophilic, metal coordination, electrostatics, covalent bonding.

Application of the biological species in the example embodiments is predominantly aqueous wet chemistry with mild conditions, thus avoiding any harsh treatment that may damage sensitive optical components (i.e. high temperature). The fabrication can represent a 'green' approach. Many techniques can be used and exist to apply biomolecules to a substrate in well-defined patterns, including ink jet printing and soft lithography. In the example embodiments, complementary biorecognition molecules or thin adhesive coatings drive the assembly of optical components onto virtually any substrate without requiring any micromachining. Biorecognition or thin adhesive coatings can allow previously incompatible materials to be integrated seamlessly on the same device. The biorecognition layer or adhesive coating may allow interesting 'soft' and 'hard' components to be integrated by themselves or as composites with the optical materials (i.e. responsive polymers and small molecules, metals, nanoparticles and objects, redox and photosynthetic proteins, ionic liquids/liquid crystals, lipid layers, cells, diatoms, silica and polymer beads etc.)

Embodiments of the present invention can provide a hybrid top-down/bottom-up strategy for producing optical structures by biomolecular assembly of high quality optical materials. Labelling the optical material with a biological receptor and the substrate with the complementary ligand (or vice versa) can allow the assembly of any optical structure on any substrate in a well defined manner. This can allow previously unrealized components to be assembled together on the same substrate. No micromachining or masking for lithography is necessary on the substrate and simple liquid transfer techniques can define the pattern (circuit geography). Using a biological assembly approach in the example embodiments can allow flexibility in substrate choice such that any planar substrate can be patterned with a biorecognition molecule for assembling optical structures. Thus, any combination of optical structures may be integrated on any material.

Assembling new materials/devices using biomolecule directed assembly or assembly using adhesive thin films of prefabricated high quality optical components was demonstrated in example embodiments. Biomolecule directed assembly of two optical structures can allow formation of a third optical structure, where the joining of the two optical structures produces a new optical characteristic in the resulting structure. Furthermore, incorporating diverse materials into assemblies with high quality optical components is possible in different embodiments towards a range of new optical materials.

INDUSTRIAL APPLICATIONS

Integrated optics. There is no current strategy that allows the integration of different optical structures onto the same substrate material. For example, the integration of III-V light sources and detectors with Si based photonic crystals, modulators and/or micro-mirrors, with waveguides and non-linear optical devices on any substrate material in example embodiments constitutes a major advance in optoelectronics.

Optical communications. Biomolecule directed self-assembly in example embodiments can allow improved and easier alignment of optical components and/or nanostructured materials on fibre optic devices.

New optical devices. The integration of many different optical components and materials together using biorecognition in example embodiments can open the door to new functional architectures and optical devices. For example, vertical cavity surface emitting lasers (VCSELs) using porous silicon mirrors and III-V spacer layers, or Er:glass spacer layer. Similarly, VCSEL type architecture with a bio-sensitized spacer layer to make very sensitive biosensors, or alternative materials into the cavity (i.e. responsive polymers and small molecules, metals, nanoparticles and objects, redox and photosynthetic proteins, molecular wires, carbon nanotubes, ionic liquids/liquid crystals, lipid layers, cells, diatoms, silica and polymer beads etc. and composites of the same) could lead to a host of novel devices, such as lasers or optical switches.

Sensors. Forming a biorecognition at the interface that is sensitive to biological species in example embodiments can enable increased biosensing sensitivity at the cavity layer in contrast to previous biosensing work that requires penetration through the mirrors.

Lab-on-a-Chip. Advances in microfluidic technologies have progressed towards realizing the integration of fluid handling, sensing and detection within a single microscale device. Embodiments of the present invention can be applied to lab-on-a-chip technologies (i.e. polycarbonate or other polymeric channels) as a method to integrate optical materials onto a device for e.g. sensing and detection.

Photovoltaics. Existing solar cells can be supplemented with high quality antireflection layers and/or back reflectors in embodiments of the present invention.

Targeted Drug delivery and Medical imaging. Fabricating assembled microparticles from porous silicon with therapeutics confined in the spacer layer with a stimuli responsive material in the embodiments of the present invention. For example, after reaching the target tissue, external (light) or internal (enzymatic, pH, etc.) stimuli causes release of the drug. Engineering the optical properties to be read through tissue (700-1000 nm) may enable monitoring drug delivery or alternatively, a method for medical imaging.

Flat-panel display fabrication, in particular light emitting diode (LEDs) or light emitting crystal (LCD) displays.

It will be appreciated by a person skilled in the art that numerous variations and/or modifications may be made to the present invention as shown in the specific embodiments.

For example, it will be appreciated that other optical characteristics of the free-standing device may be substantially maintained after assembly, other than the transmission/reflectance spectra described for the example embodiments, and including, but not limited to, optically tested characteristics of non-optical devices for substantially maintaining machining tolerances, such as optical interference based characterisation for assembly of micro mechanical or micro electro mechanical systems (MEMS) on a substrate.

Figure 14:
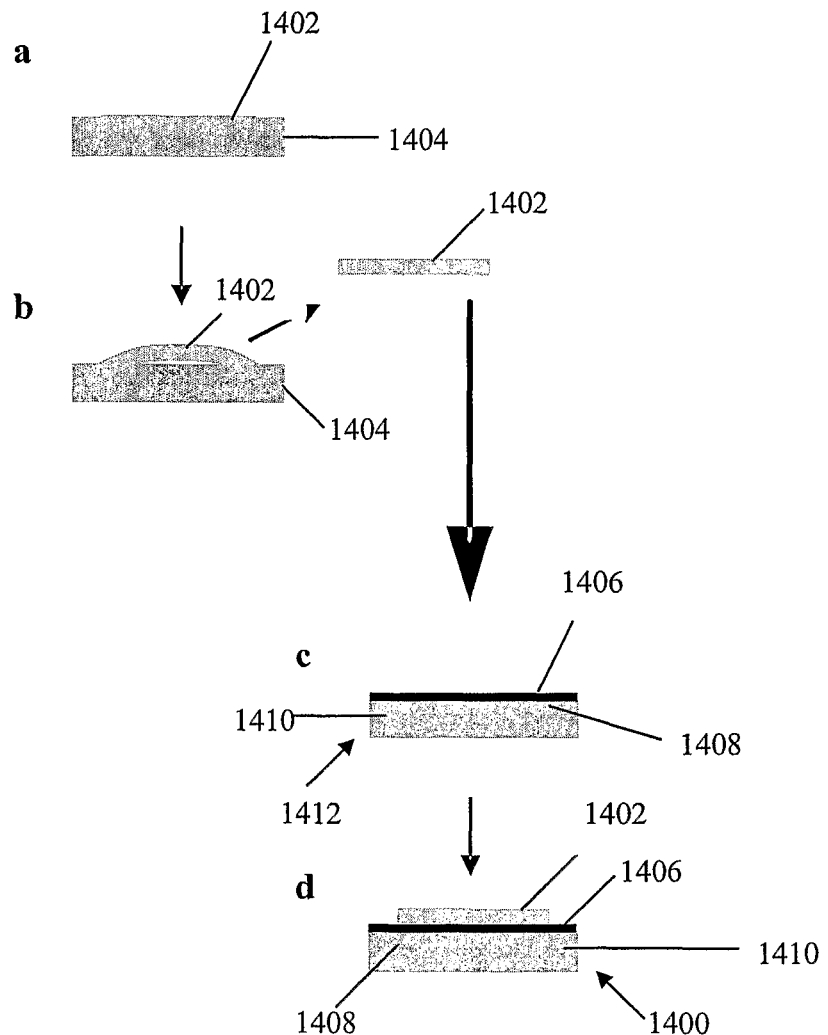
FIGS. 14a-d show schematic cross-sectional drawings illustrating fabrication of a sensor structure according to an embodiment of the present invention.

FIG. 14 shows schematic cross-section drawings illustrating fabrication of a sensor structure 1400 according to an embodiment of the present invention. This sensor structure 1400 for detecting stimuli is composed of a stimuli responsive material 1406 (spacer material) between two PSi Bragg mirrors 1402 and 1408 such that the spacer material 1406 defines the position of the cavity resonance. While two PSi Bragg mirrors 1402 and 1408 are illustrated for the example embodiment, it will be appreciated that the Bragg mirrors in different embodiments can be formed from different materials. Furthermore, different material Bragg mirrors may be used in a single device on the top and the bottom of the spacer material, for example to extend the optical Bragg plateau.

Figure 15:
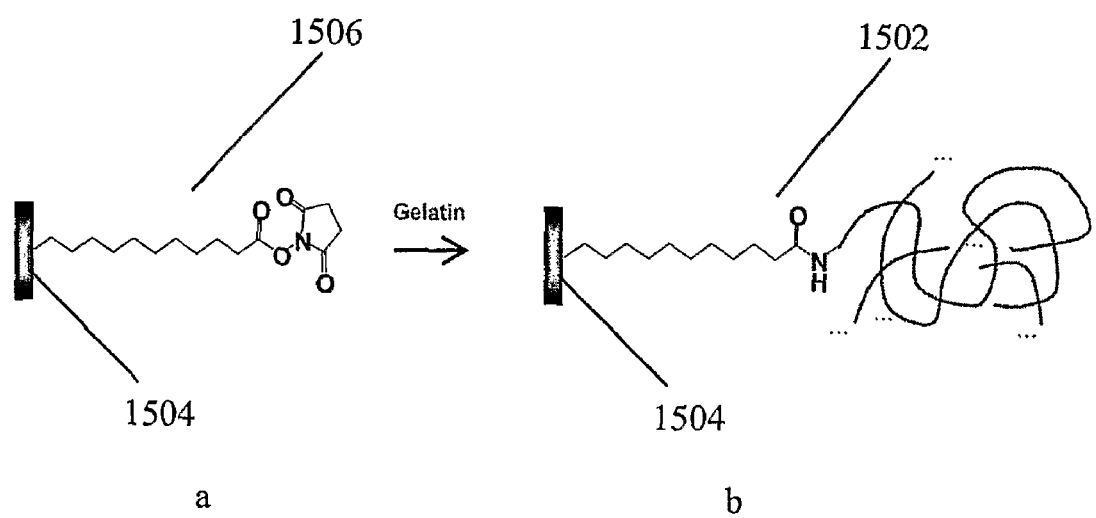
FIGS. 15a and b show schematic cross-sectional drawings illustrating the coating of a spacer material onto a surface of a Bragg mirror according to an embodiment of the present invention.

PSi Bragg mirrors 1402 and 1408 are formed by anodizing crystalline silicon in ethanolic hydrofluoric acid solution with a step function to yield alternating layers of high and low refractive index (porosity). It will be appreciated that other techniques may be used for fabrication of the Bragg mirrors, including, but not limited to, other electrochemical techniques with different combinations of electrolyte, doping level and type, and processing conditions. The PSi surfaces 1402 and 1408 can either be used 'as prepared' or are derivatized. In this example embodiment, the surfaces 1402 and 1408 are by hydrosilylation of the functional alkene 10-succinimidyl undecenoate 1502 to stabilize the material and provide a functional group for further modification as shown in FIG. 15. Details of further modification provided by the functional group can be found in K. A. Kilian, T. Böcking, K. Gaus, M. Gal, J. J. Gooding, *Biomaterials* 2007, 28, 3055., K. A. Kilian, T. Böcking, K. Gaus, J. J. Gooding, *ACS Nano* 2007, 1, 355., K. A. Kilian, T. Böcking, K. Gaus, J. KingLacroix, M. Gal, J. J. Gooding, *Chemical Communications* 2007, 1936., K. A. Kilian, T. Böcking, S. Ilyas, K. Gaus, M. Gal, J. J. Gooding, *Advanced Functional Materials* 2007, 17, 2884. and K. A. Kilian, T. Böcking, L. M. H. Lai, S. Ilyas, K. Gaus, M. Gal, J. J. Gooding, *International Journal of Nanotechnology* 2007, 5, 170, the contents of which are incorporated herein by cross-reference.

In one example, the steps of fabricating the sensor structure 1400 are illustrated in FIG. 14 (14a-14d). In FIG. 14a, a Bragg mirror 1402 is formed on a substrate 1404. In FIG. 14b, the Bragg mirror 1402 is lifted off the substrate 1404 to form a free-standing component using a short pulse of high current density.

FIG. 14c shows forming a separate Bragg mirror 1408 on a separate substrate 1410 and coating a thin film of a spacer material 1406 onto the surface of the Bragg mirror 1408.

In FIG. 14d, the Bragg mirror 1402 lifted off the substrate 1404 is assembled onto the spacer material 1406 forming the sensor structure 1400 with the spacer material 1406 between the Bragg mirror 1402 and the Bragg mirror 1408. The process depicted in FIG. 14 forms a sandwich of polymeric material that functions as a microcavity.

FIG. 15 shows a schematic cross-sectional drawing illustrating the process of coating a gelatin spacer material 1502 onto a Bragg mirror surface 1504 according to an embodiment of the present invention. In FIG. 15a, the Bragg mirror surface 1504 is derivatized by hydrosilylation of the functional alkene 10-succinimidyl undecenoate 1506 and in FIG. 15b, the gelatin spacer material 1502 is further coated onto the Bragg mirror surface 1504. The derivatization process in this example embodiment prevents the gelatin spacer material 1502 from infiltrating into the Bragg mirror surface 1504. It is noted that the derivatization of the Bragg mirror surface 1504 in this example embodiment is optional, since the unmodified Bragg mirror surface is hydrophobic, thus already inhibiting easy penetration of the spacer material. Applying the derivatization process can provide additional surface protection for the Bragg mirror surface, and may provide increased functionality of the Bragg mirror surface. Furthermore, it is noted that the derivatization process may also be applied to the lifted off ("upper") Bragg mirror 1402 (FIG. 14) in different embodiments, noting that typically it is less important to passivate the upper mirror against infiltration because the spacer material, for example gelatin, is typically allowed to solidify before the upper mirror is deposited.

Figure 16:
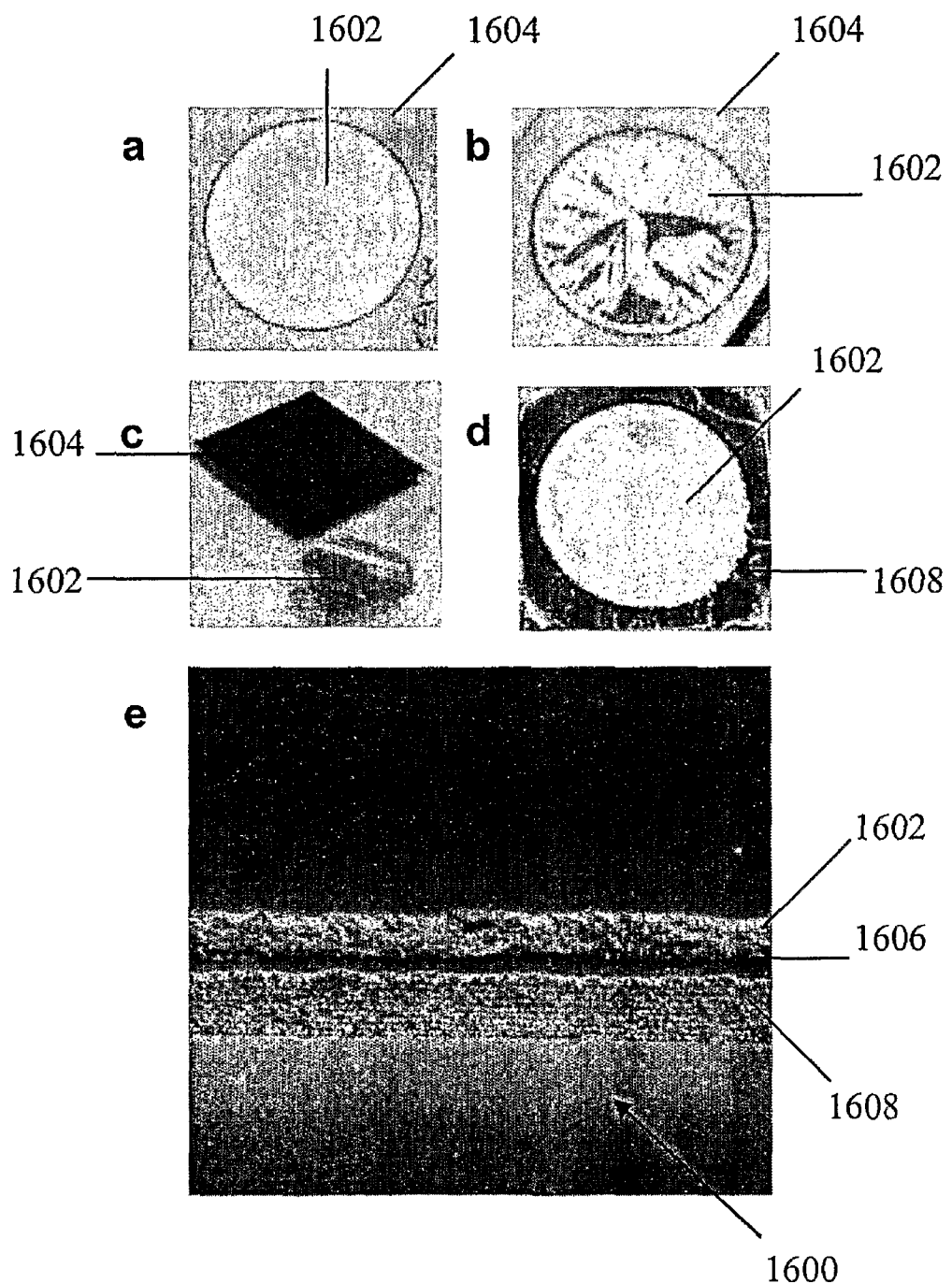
FIGS. 16a-e show photographs of the different stages in the formation of a sensor structure and a scanning electron microscope image of the sensor structure according to an embodiment of the present invention.

FIGS. 16a-16d shows photographs of different stages in the process of forming a sensor structure 1600 according to an embodiment of the present invention. FIG. 16a shows the appearance of a freshly prepared PSi Bragg mirror 1602 on the substrate 1604, after anodization wherein the colour of the material (shown as different shades) is directly related to the etching parameters. After the electrochemical lift off of the Bragg mirror 1602 from the substrate 1604, the film of Bragg mirror 1602 is flexible as shown in FIG. 16b. This film 1602 can be mechanically removed from the substrate 1604 as shown in FIG. 16c. In FIG. 16d, spin-coating thin films of polymer results in a uniform coating of the gelatin (not shown in FIG. 16d) onto the base Bragg mirror 1608 of which the colour is dependent on the thickness of the layer as indicated by different shades. Successful adhesion of the lift-off Bragg mirror 1602 by interaction of the Bragg mirror 1602 (a hydrophobic PSi film) with the structure (consisting of the base Bragg mirror 1608 and the gelatin) is shown by the appearance of the film 1602 in the lighter shade above the base Bragg mirror 1608. In this case, complete and high quality adhesion is evident from the absence of a rumpled appearance to the film 1602. Further, the quality of adhesion can be readily verified by reflectivity spectroscopy. It is preferable to achieve a high quality and complete adhesion as a non-uniform adhesion can result in a Bragg mirror spectrum without any cavity resonance. In this case, the scanning electron microscopy of the sensor structure 1600 as shown in FIG. 16e is consistent with uniform and parallel adhesion as evidenced by a thin film of gelatin 1606 sandwiched between two PSi Bragg mirrors 1602 and 1608.

Figure 17:
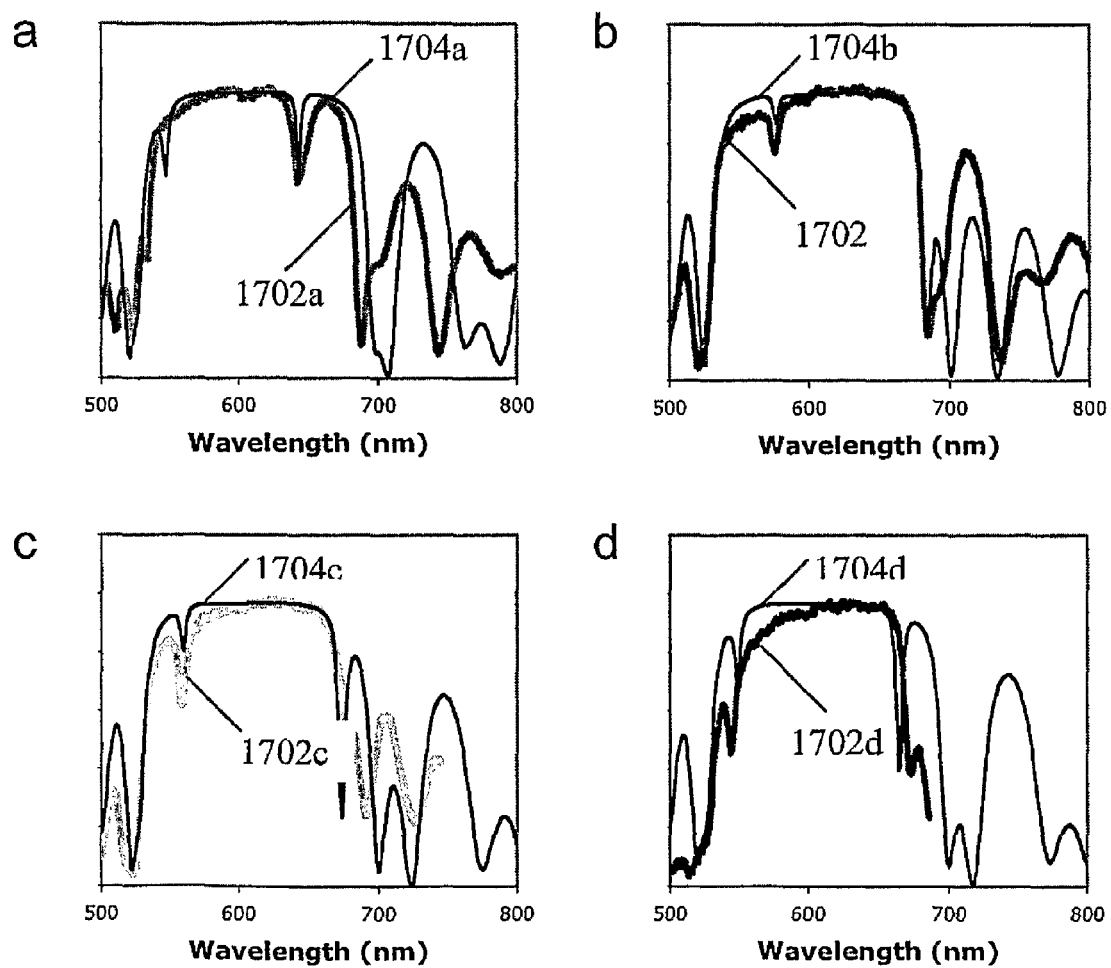
FIGS. 17a-d show graphs illustrating optical reflectance spectra of sensor structures according to different embodiments of the present invention.

FIG. 17 shows graphs illustrating the optical reflectance spectra of a sensor structure containing sandwich microcavities with PSi Bragg mirrors and gelatin spacer layer according to different embodiments of the present invention. In these embodiments, the optical thickness of the gelatin film was adjusted by using different concentrations of gelatin (FIG. 17a—10 mg/mL, FIG. 17b—17 mg/mL, FIG. 17c—2.5 mg/mL, FIG. 17d—1.25 mg/mL). The optical properties of the Bragg mirrors used in the fabrication of the different structures in FIG. 17a-17d are identical and hence the Bragg plateau spans the same region of the optical spectrum from approximately 1730 nm to 690 nm. The pronounced differences in the resonance peak positions as shown in curves 1702a, 1702b, 1702c and 1702d were achieved by tuning the optical thickness of the gelatin spacer layer. In general the optical thickness (n·d) of the spacer layer may be adjusted by altering its refractive index (n), for example, by changing its composition, or by altering its thickness (d). In the example in FIG. 17, the optical thickness of the spacer layer was tuned by adjusting the concentration of the gelatin solution used in the spin coating step from 1.25 mg/mL up to a concentration of 10 mg/mL. The approach is validated by the simulations of the structures using an effective medium model in which the optical properties of the Bragg mirrors were fixed and only the optical thickness of the spacer layer was adjusted to fit the experimental curves 1702a, 1702b, 1702c and 1702d. The spacer layer optical thickness used in the simulations decreases from FIG. 17a to FIG. 17d since it is expected that the spacer layer optical thickness would decrease for decreasing gelatin concentrations. The results of the simulations are shown as curves 1704a, 1704b, 1704c and 1704d. In these examples, the thickness of the spacer layers ranges from approximately 100 nm (for the structure prepared with 1.25 mg/mL gelatin solution) to 300 nm (for the structure prepared with 10 mg/mL gelatin solution) assuming a refractive index of 1.4 for the gelatin layer. The positions of the experimentally measured cavity resonances in curves 1702a, 1702b, 1702c and 1702d are in good agreement with those of the simulations in curves 1704a, 1704b, 1704c and 1704d. The good agreement between experimental and theoretical results demonstrates the high quality of the sensor structure fabricated by the general approach introduced in FIG. 14.

The operation of the sensor structure in the example embodiments can be illustrated by experimental results discussed below with reference to FIGS. 18-21.

Figure 18:
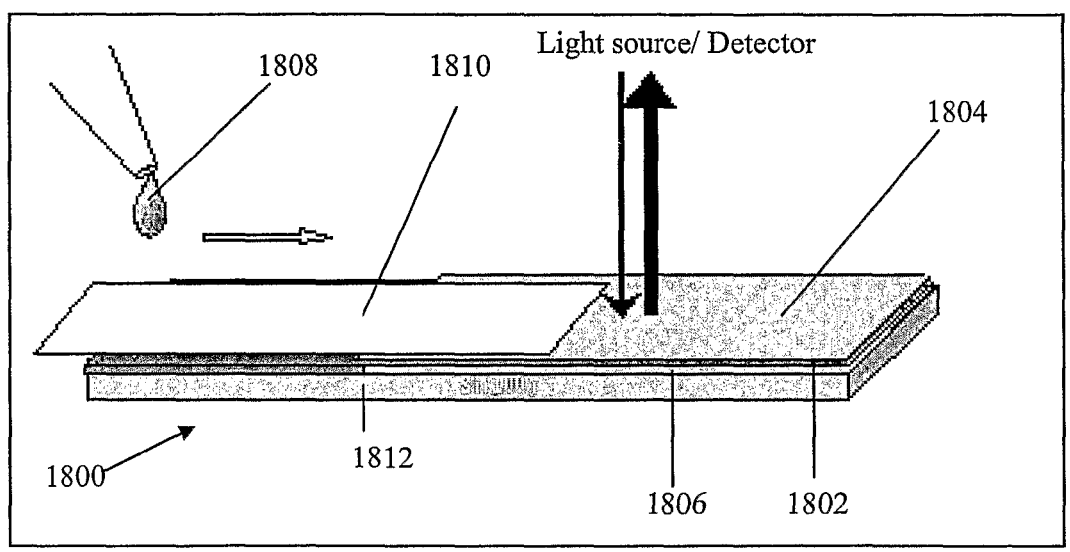
FIG. 18 shows an experimental setup for a sensing application of a sensor structure according to an embodiment of the present invention.

FIG. 18 illustrates the experimental setup for detecting protease enzymes using the sensor structure 1800 according to an embodiment of the present invention. In FIG. 18, a gelatin film 1802 that can be reproducibly cast between the Bragg mirrors 1804 and 1806 at different thicknesses using spin-coating is shown. The gelatin film 1802 lies on top of the substrate 1812. Application of protease enzyme 1808 to a thin strip of filter paper 1810 causes rapid degradation of the gelatin 1802 i.e. proteolysis of the gelatin thin film 1802. The reaction is directly with the spacer layer. The material is not entering the two Bragg reflectors. As discussed above, the mirror surfaces are hydrophobic, thus inhibiting easy penetration by the spacer material. If the material was to enter the pores of the mirrors a red shift would be observed because the average refractive index of the structure has been increased. Note that the operation of the biosensing mechanism effectively destroys the cavity layer, thus leading to a blue shift. Therefore if water vapour was entering the mirror pores the resultant red shift due to air being replaced by water would mask this blue shift.

Figure 19:
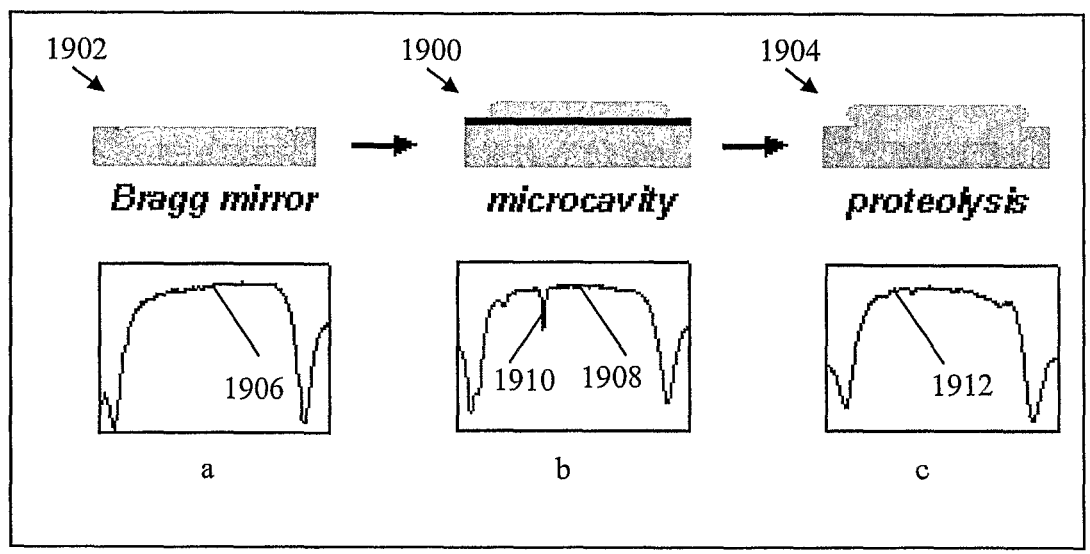
FIGS. 19a-c show experimental results using the experimental setup in FIG. 18 according to an embodiment of the present invention.

FIG. 19 shows schematic cross-section drawings and spectra depicting the results obtained using the experimental setup in FIG. 6. In FIG. 19a, the optical reflectance spectrum of a Bragg mirror 1902 is shown whereby the spectrum contains a Bragg plateau 1906. In FIG. 19b, the optical reflectance spectrum of the assembled microcavity structure 1900 before proteolysis is shown whereby the spectrum contains a Bragg plateau 1908 and a cavity resonance 1910. In FIG. 19c, the optical reflectance spectrum of the structure 1904 (structure 1900 after proteolysis) is shown whereby the cavity resonance 1910 disappears whereas the position of the Bragg plateau 1912 remains the same. Disappearance of the cavity resonance in this example is caused by complete digestion of the spacer layer such that the periodicity of the Bragg mirror is no longer interrupted. Partial proteolysis would be evident by a shifting of the position of the cavity resonance to different wavelengths reflecting the changes in the optical thickness of the spacer layer (resulting from a change in refractive index or thickness or both).

In contrast to previous sensing work, interactions within the spacer layer 1406 (FIG. 14) in the above example embodiments affect only the position and magnitude of the resonance without changing the position of the Bragg plateau (high reflectivity region). This is because the system in the above example embodiments is designed in such a way that the analyte of interest, for example an enzyme, interacts only at the spacer layer 1406 (FIG. 14) and does not infiltrate the nanopores of the PSi nanoporous structure 1408 by keeping the pore space hydrophobic. Further details of keeping the pore space hydrophobic in the nanoporous structure 1408 (FIG. 14) can be found in K. A. Kilian, T. Böcking, K. Gaus, J. J. Gooding, *Angew. Chem. Int. Ed.* 2008, 47(14), 2697-2699 the contents of which are incorporated herein by cross-reference.

Figure 20:
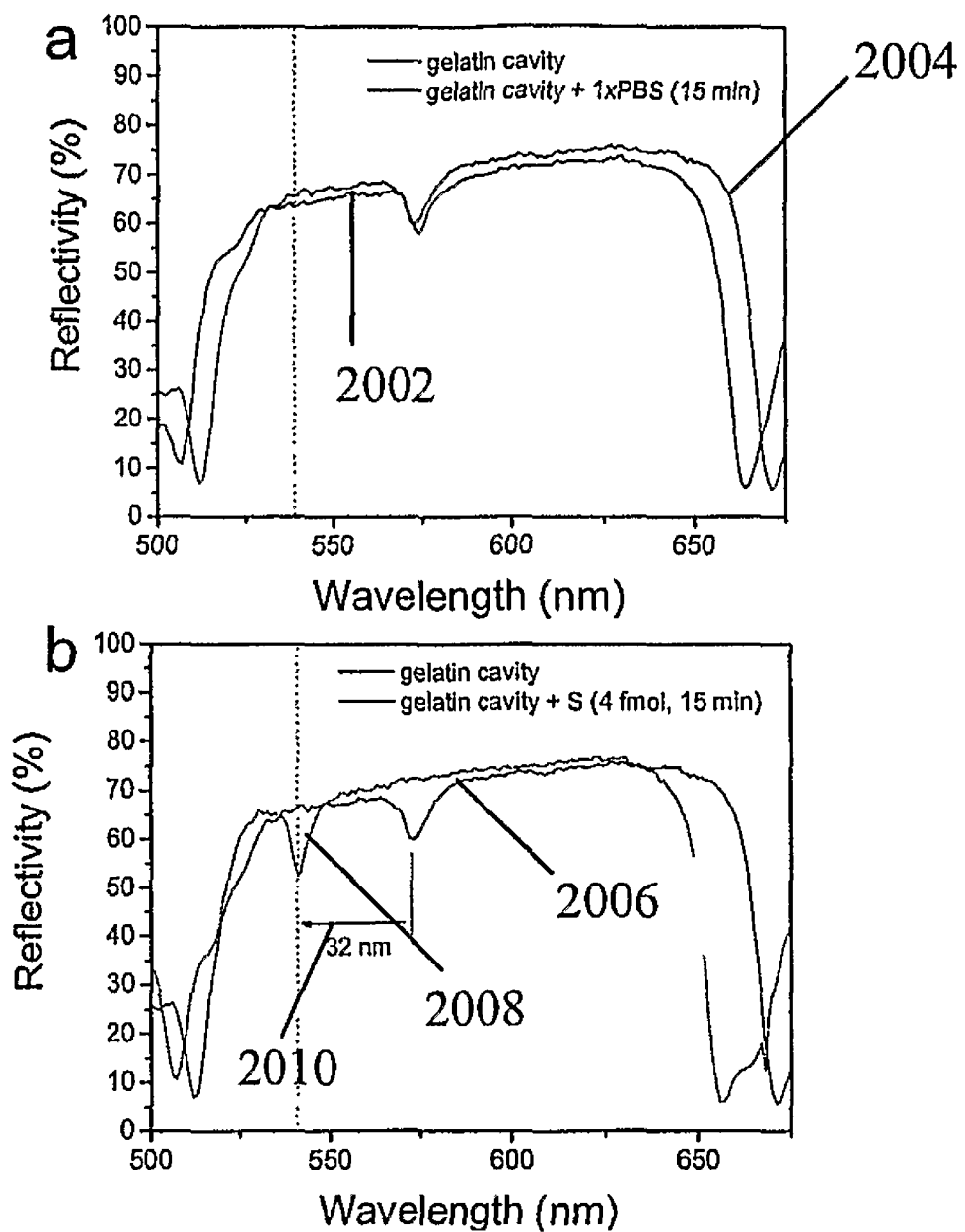
FIGS. 20a and b show further experimental results using the experimental setup in FIG. 18 according to an embodiment of the present invention.

FIG. 20 shows further experimental results using the experimental setup in FIG. 18 according to an embodiment of the present invention.

The Bragg mirror was adhered to the gelatin layer by allowing the PSi to come into close contact with the gelatin under ethanol and the resulting sandwich was allowed to dry under a slip of filter paper in ambient air. After drying, a well-defined cavity resonance appears central to the Bragg plateau as shown in curve 2002 in FIG. 20a. Next, a small quantity of phosphate buffered saline was added to the sample by applying a 5 μl drop to a piece of filter paper adhered to the top mirror. The fluid wicked up the paper to make contact with the spacer layer and was incubated for 15 minutes until the paper became dry. Measuring the spectrum at the same location after buffer addition resulted in a negligible change to the spectral qualities of the sample as shown in curve 2004 in FIG. 20a.

In FIG. 20b, curves 2006 and 2008 respectively illustrate the optical reflectance spectra before and after the addition of an enzyme (5 μl of 1 nM subtilisin (5 fmoles)). It can be seen that this addition resulted in a large shift (32 nm) of the photonic resonance (curve 2008) compared to the control position (curve 2006) as indicated by arrow 2010.

FIGS. 20a and b show that the addition of the enzyme has resulted in a shift of the gelatin resonance position by enzymatic digestion of the film. This shows that the sensor structure in the example embodiments works effectively as a sensing device for stimuli such as the protease enzyme.

Figure 21:
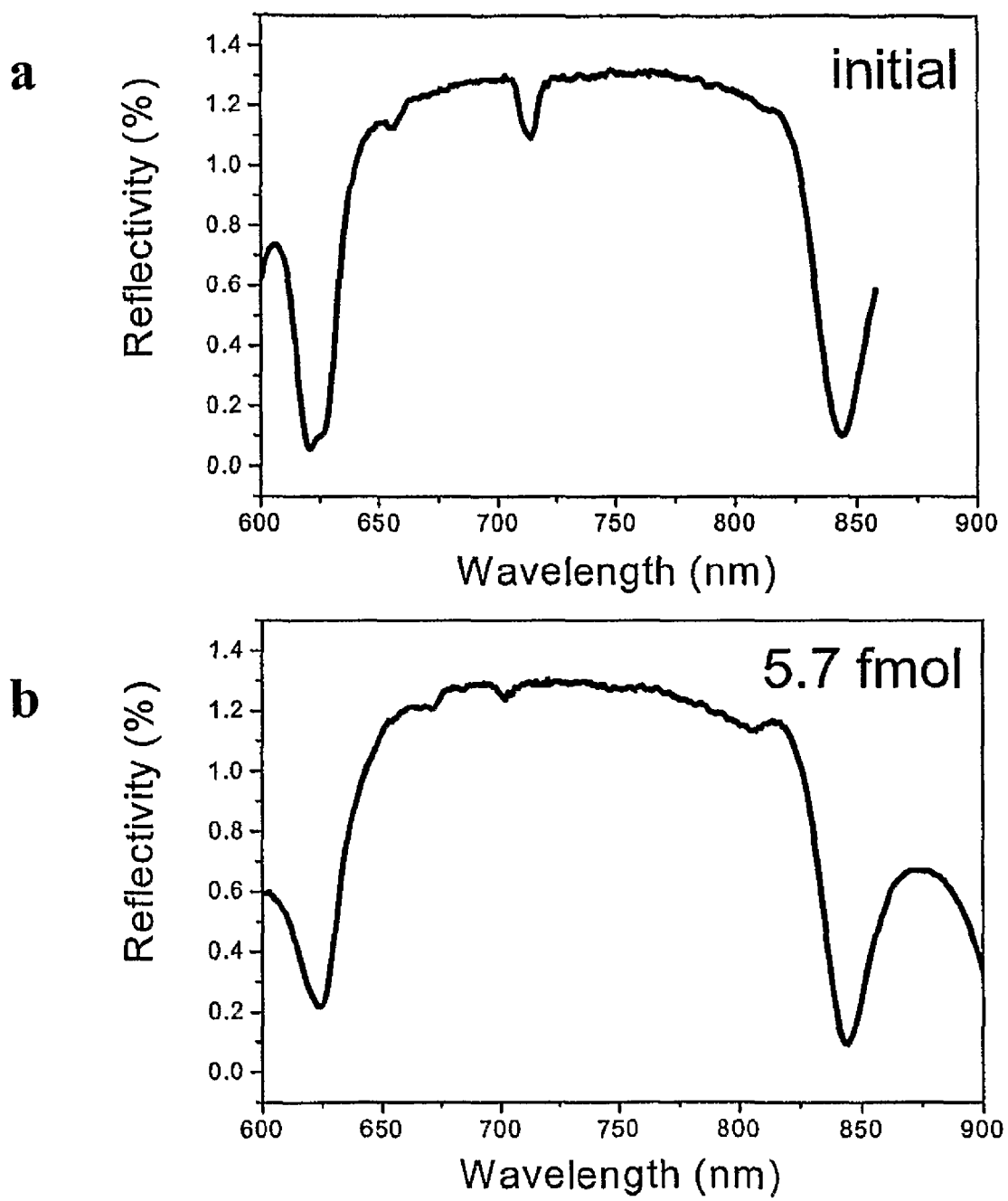
FIGS. 21a-b show the optical reflectance spectra before and after proteolysis occurs in a sensor structure according to an embodiment of the present invention.

FIG. 21 shows the optical reflectance spectra before and after proteolysis occurs in a sensor structure according to an embodiment of the present invention. The optical reflectance spectra before and after proteolysis are shown in FIGS. 21a and 21b respectively. In this example, the gelatin layer remaining between the top and bottom Bragg mirror after proteolysis is negligible (ie it has essentially been digested) such that proteolysis results in complete disappearance of the cavity resonance as shown in FIG. 21.

Figure 22:
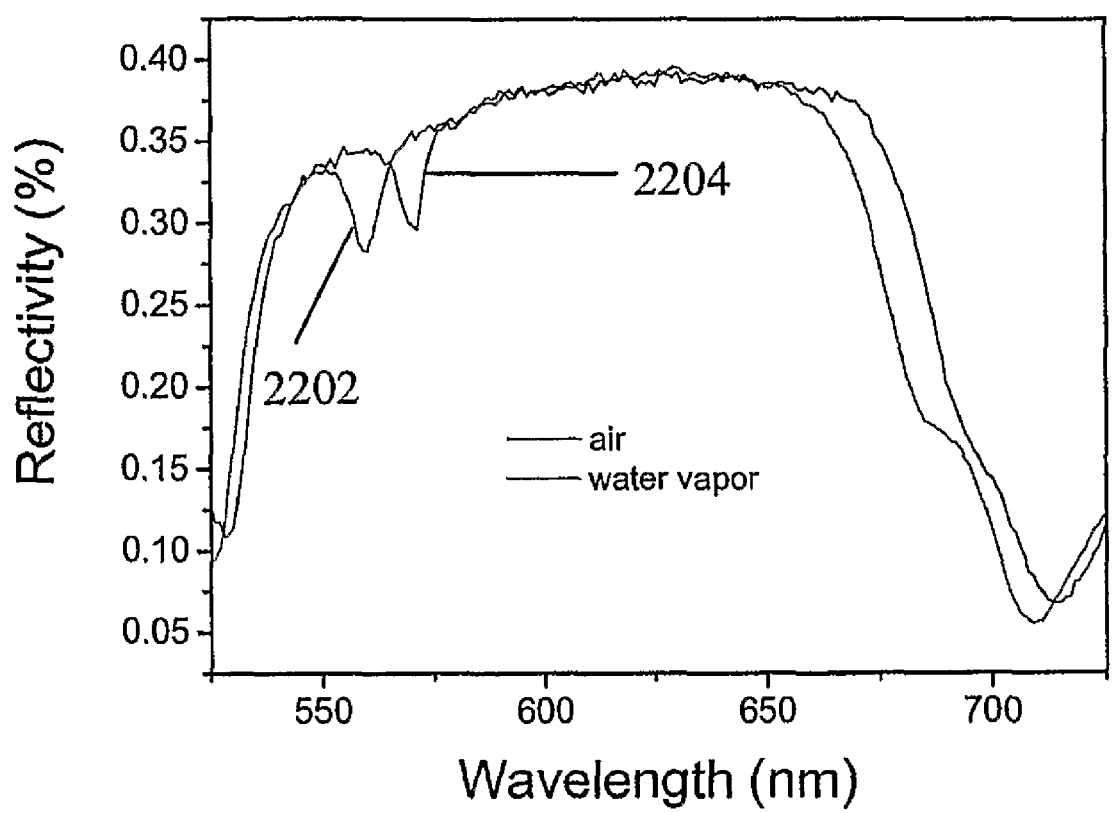
FIG. 22 shows a plot illustrating the shift in the optical spectrum after exposure of a sensor structure to water vapour according to an embodiment of the present invention.

FIG. 22 shows a plot illustrating the shift in the optical spectrum after exposure of a sensor structure to water vapour according to an embodiment of the present invention. After exposing the gelatin microcavity to water vapour, there is a distinct red shift (9 nm normalized to the shift in Bragg plateau) in the position of the cavity resonance as the gelatin swells by incorporating water molecules within the hydrogel layer. This is shown in the shift from curve 2202 to curve 2204 in FIG. 22. This shift is evident visually by a change in the color of the thin film as it swells. In contrast to organic vapor sensing, the Bragg plateau remains at approximately the same position due to the hydrophobic surface disallowing any influx of water molecules.

In other embodiments, by monitoring the change in the Bragg plateau, detection of species that do penetrate hydrophobic spaces could be assessed. For example, exposure to ethanol can cause a predictable shift of the entire Bragg plateau as the surface tension of ethanol allows it to penetrate a hydrophobic nanoporous material. Concurrently monitoring the position of the cavity resonance that is sensitive to materials that only interact in the spacer layer may allow simultaneous detection of different species by separating the spectrum into changes in the cavity resonance or Bragg plateau. In this way, surface chemistries and spacer layers that respond to different chemicals and stimuli could be applied to this device in the example embodiments, allowing multi-analyte sensing.

Furthermore, in alternative embodiments the surface chemistry of the top and bottom optical materials may be tailored so as to allow flexibility in design. For instance, this can be done by allowing water or organic solutions to penetrate the porous silicon via tailored surface chemistry or by providing recognition elements within or on the top or between sensor structures.

In other example embodiments, different passive optical materials such as microcavities, filters, waveguides, etc. can also be joined together with a wide variety of functional materials such as photo, thermal and pH responsive polymers and small molecules (dyes) in polymer matrices, metals, semiconductors, nano and micro particles and objects, quantum dots, redox and photosynthetic proteins, viral capsids, self-assembling biomolecules, carbon nanotubes, buckyballs etc. The joining of many different optical materials that may work alone or synergistically can convey single or multiple recognition events.

Figure 23:
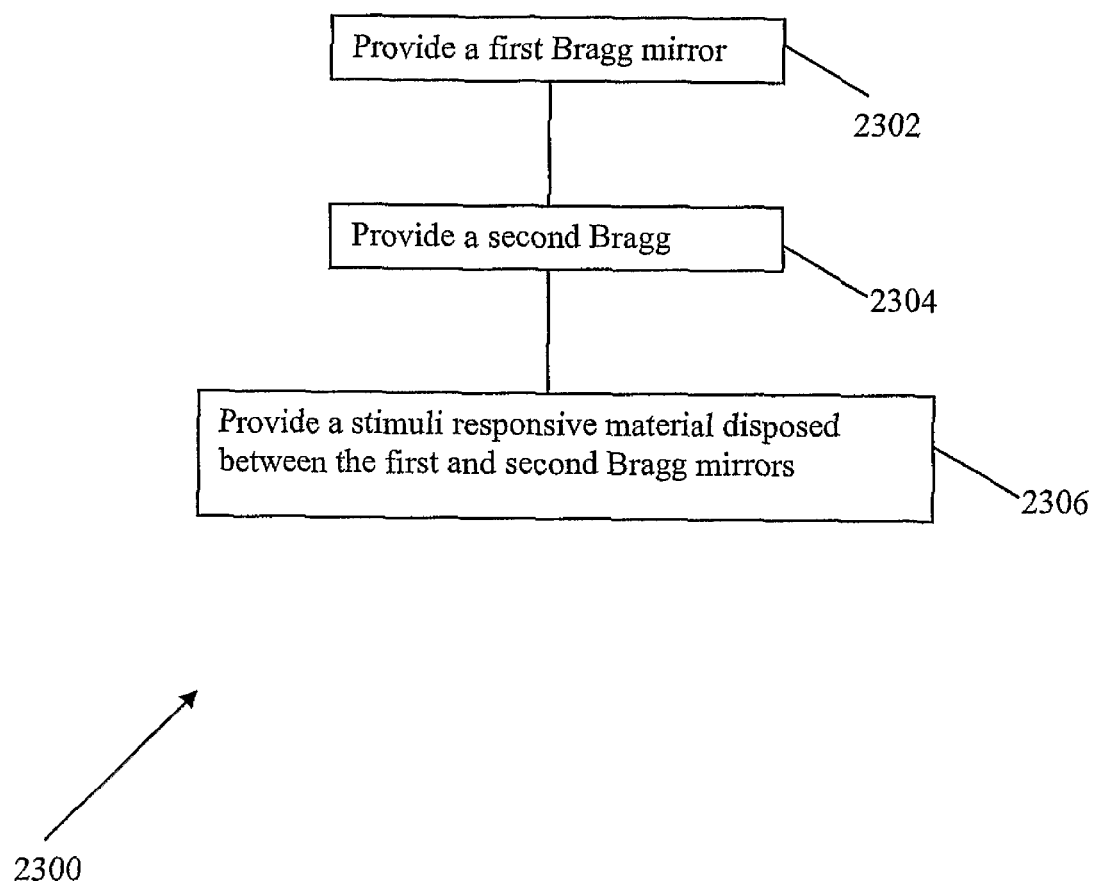
FIG. 23 shows a flow chart illustrating a method of fabricating a sensor structure according to an embodiment of the present invention.

FIG. 23 shows a method 2300 of fabricating a sensor structure according to an example embodiment. In step 2302, a first Bragg mirror is provided. In step 2304, a second Bragg mirror is provided and in step 2306, a stimuli responsive material disposed between the first and second Bragg mirrors is provided. The second Bragg mirror is assembled on the first Bragg mirror by a binding interaction via the stimuli responsive material.

The advantages of the embodiments of the present invention can include:

The detection limit of less than 10 fmoles (i.e. the least amount of stimuli required to produce a detectable output, in this case loss of the cavity resonance) using the embodiments of the present invention is 1000-fold greater than other existing label-free optical approaches.

Also, the assay setup in the example embodiments is simple without any labelling requirements. Only the employment of a simple light source and detector is necessary. This allows the device in the example embodiments to be in a portable format and be easily used by a simple application of fluid. The device can also be designed to yield a colour change visible by the naked eye, allowing it to be more user-friendly.

In addition, the device in example embodiments can allow a faster and a more sensitive optical detection of molecules as compared to prior art devices. In one example, it can detect low levels of biological species within only 15 minutes. The high speed and high sensitivity are achieved in the example embodiments as sensing occurs at the interface between two optical materials, thus reducing the recognition area to a path on the order of the wavelength of light. This means that transduction of recognition and response occurs more rapidly and the sensitivity to the analyte is increased. Furthermore, fast and sensitive optical detection of molecules can be achieved In the example embodiments, because the stimuli responsive material is accessible from the sides, there is no requirement of analyte diffusion through the Bragg mirror to reach the stimuli responsive material, which can decrease the response time compared to existing sensor structures.

On the other hand, modifying the base layer (Bragg mirror) with one or more specific chemistry for an analyte of interest, incorporating a cavity layer that responds to a different recognition or stimuli, and/or modifying the top layer (Bragg mirror) with another specific chemistry or chemistries in different embodiments can allow two or more separate responses that can be deconvoluted to provide information about multiple interactions and/or stimulations.

The device in the example embodiments can be fabricated with low cost materials. Patterning of the materials is well established, involves inexpensive materials and is amenable to self-assembly strategies. In addition, complementary biorecognition molecules can drive the assembly of optical components onto virtually any substrate without requiring any micromachining.

Also, in the example embodiments, optically flat adhesion using protein-based adhesive can enable many different combinations of sensor structures and other materials across a surface (patterning) and vertically to realize novel hybrid materials that respond in a well-defined way to various chemicals and stimuli. For example, patterning Bragg mirrors across a surface with a specific chemistry (covalent, hydrophobic, ionic, H-bonding) can allow precise deposition of responsive material to form the cavity. Alternatively, photolithography may allow patterning of a polymeric (or hybrid) material spatially across an optical material for subsequent recognition and assembly of another optical material.

Applications of the device in the example embodiments further include the use of the device as a biological sensor, chemical sensor, temperature, light, pH, voltage or mechanical sensor or as integrated optics for a Lab-on-a-Chip. When using the device in the example embodiment as a biological sensor, detecting biomolecules within the cavity layer between PSi sensor structures can enable faster detection with enhanced sensitivity without any requirements for infiltration within nanopores. When the device is used as a chemical sensor, detection of chemical species can occur within the PSi crystals or within the cavity layer. Tailoring the cavity material and the surface chemistry of the PSi to respond to one or multiple species will enable multiplexed analysis. In addition, incorporating responsive materials in the cavity will allow detection of other stimuli when the device in the example embodiments is used as a temperature, light, pH, voltage or a mechanical sensor. Furthermore, the responsive materials in the example embodiments can be integrated into microfluidic circuits with detectors for lab-on-a-chip type applications.

It will be appreciated by a person skilled in the art that numerous variations and/or modifications may be made to the present invention as shown in the specific embodiments.

For example, the stimuli responsive material may comprise one or more of a group consisting of gelatin, extracellular matrix biopolymers, proteins, oligosaccharides, proteoglycans, recombinant polypeptides, synthetic polypeptides, nucleic acids, synthetic co-polymer systems, small molecule and nano-object encapsulated polymers, pNIPAM, lipids, carbohydrates, cellulose, cells, plant or animal tissue, polymers of any type, hydrogels, microorganisms, nanoparticles or nanowires.

Furthermore, the surface of one or both of the Bragg mirrors may be derivatized using one or more of a group consisting of succininide ester, carboxylic acids, Amines, Maleimides, Epoxides, Azides, Alkynes, alcohols, carbodiimides, aldehydes, diazoniums, imines, acid chlorides, disulfides, and anhydrides.

Figure 24:
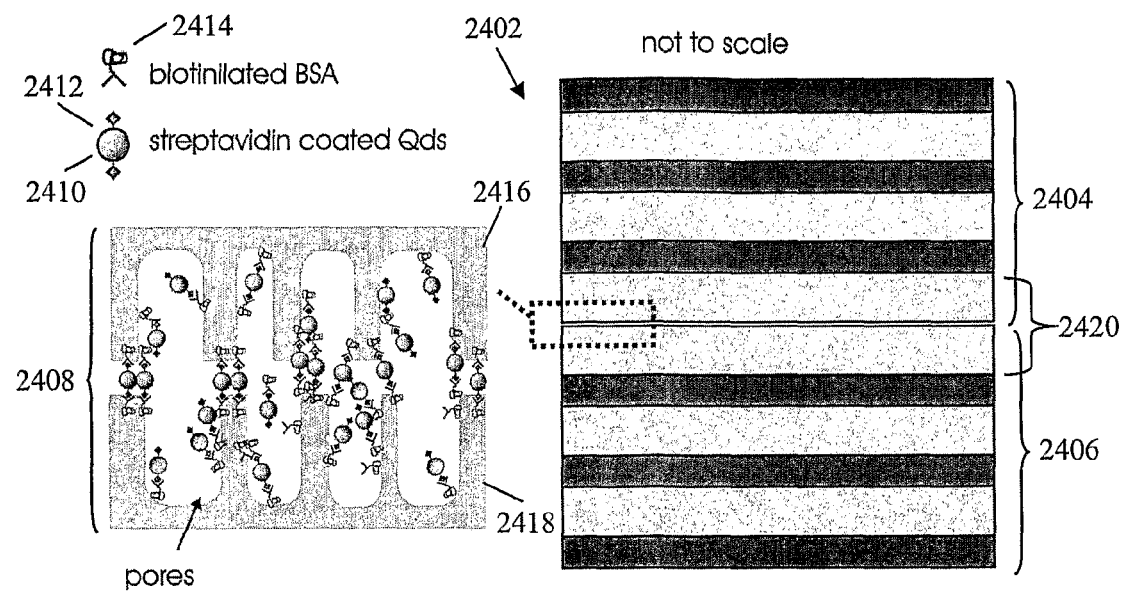
FIG. 24 shows a schematic cross-sectional view of a light emitting device according to an example embodiment.

FIG. 24 shows a schematic cross-sectional view of a light emitting device 2402 according to an example embodiment. The light emitting device 2402 comprises an upper Bragg mirror 2404 bound on a lower or substrate Bragg mirror 2406 through a binding interaction via a light emitting material 2408. The light emitting material 2408 comprises quantum dots (QDs), in the example embodiment colloidal QDs 2410. The QDs 2410 are bound within the light emitting material 2408 via pairs of biorecognition elements, e.g. 2412, and complimentary species, e.g. 2414. The light emitting material 2408 in the example embodiment is diffused into respective interfacial regions 2416, 2418 of the Bragg mirrors 2404, 2406 respectively, such that the interfacial regions 2416, 2418 form a host for the light emitting material 2408 including the QDs 2410. An optical cavity 2420 is formed by the adjacent interfacial regions 2416, 2418.

In the following, the fabrications steps for the light emitting device 2402 in an example embodiment will be described.

The substrate Bragg mirror 2406 (low porosity 44%/high porosity 80%) was formed from a p+ type silicon with a top high porosity layer. The Bragg mirror 2406 was spotted for 5 minutes with biotinylated BSA, rinsed with PBS, and then spotted for 5 minutes with a solution containing streptavidin conjugated CdSeTe/PbS colloidal quantum dots, followed by a final rinse.

The upper Bragg mirror 2404 was fabricated with an inverted structure on a separate silicon substrate, and lifted off the silicon substrate. Biotinylated BSA was again applied to the Bragg mirror 2404, and then the Bragg mirror 2404 was attached, creating a high porosity cavity or spacer layer (compare interfacial regions 2416, 2418) with the light emitting material, including the QDs, in the center.

Figure 25:
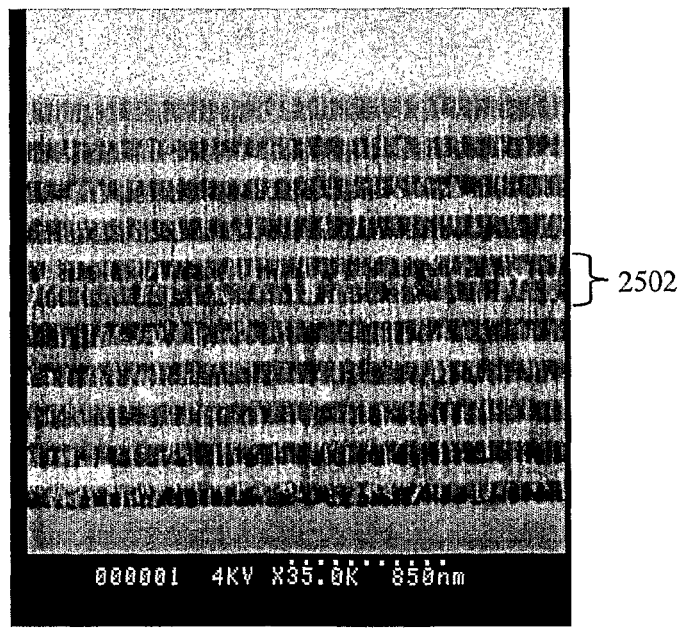
FIG. 25 shows a scanning electron microscopy (SEM) image of the fabricated structure in an example embodiment.

FIG. 25 shows a scanning electron microscopy (SEM) image of the fabricated structure in an example embodiment, illustrating the high porosity cavity or spacer layer 2502 with the light emitting material, including the QDs, in the center (not resolved in FIG. 25).

Figure 26:
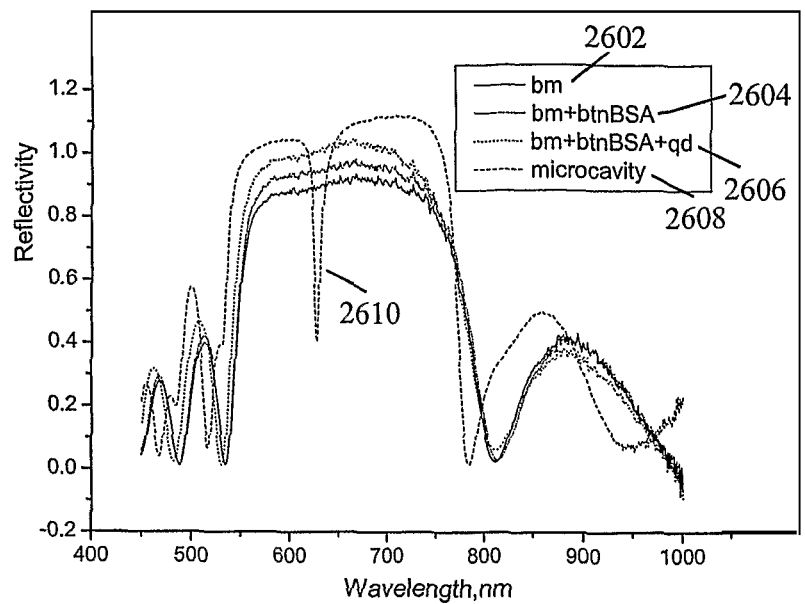
FIG. 26 shows reflectance spectra measured for different stages of the fabrication of the light emitting device of the example embodiment.

FIG. 26 shows reflectance spectra measured for different stages of the fabrication of the light emitting device of the example embodiment. Curve 2602 is the reflectance spectrum obtained from the bottom or substrate Bragg mirror 2406 (FIG. 24). Curve 2604 shows the reflectance spectrum for the Bragg mirror 2406 (FIG. 24) after spotting with the biotinylated BSA. Curve 2606 shows the reflectance spectrum of the Bragg mirror 2406 (FIG. 24) after spotting with the streptavidin conjugated CdSeTe/PbS colloidal quantum dots. Finally, curve 2608 shows the reflectance spectrum of the entire light emitting device 2406 (FIG. 24), with the cavity resonance mode 2610 at about 627.5 nm. The thickness of the high porosity cavity layer (compare 2502 in FIG. 25) was chosen in the example embodiment to match the emission wavelength of the quantum dots at about 625 nm.

Figure 27:
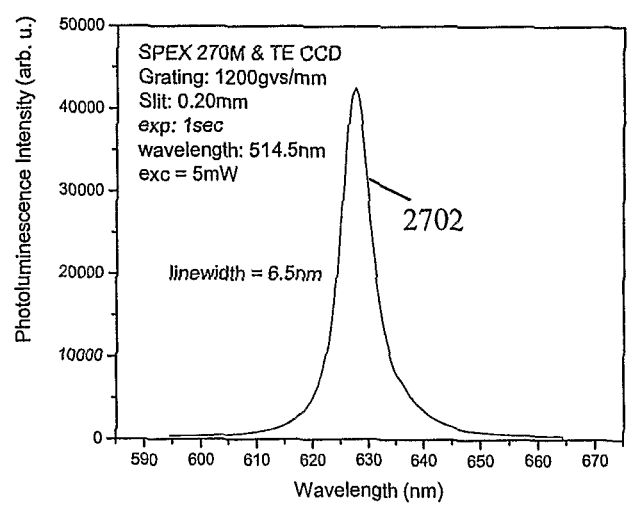
FIG. 27 shows the measured photo luminescence of the light emitting device of the example embodiment.

FIG. 27 shows the measured photo luminescence of the light emitting device for the example embodiment. For the measurement shown in FIG. 27, the light emitting device was optically pumped using an argon ion laser with a wavelength of 514.5 nm, at 5 mW. The high resolution photo luminescence measurement (curve 2702) shows a strong QD emission from the optical cavity, with a linewidth of the emission band of about 6.5 nm, which is consistent with the linewidth of the cavity mode as measured in the reflectivity spectrum (compare curve 2608 in FIG. 26).

Figure 28:
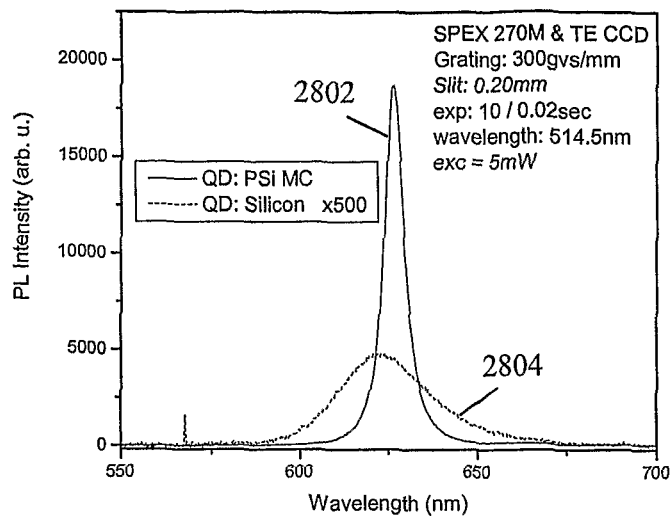
FIG. 28 shows a comparison of the photo luminescence measured for the example light emitting device of the example embodiment, with a photo luminescence measurement for the same QDs deposited on silicon using the same fabrication times.

FIG. 28 shows a comparison of the photoluminescence measured for the example light emitting device in curve 2802, with a photo luminescence measurement for the same QDs deposited on silicon using the same fabrication times, in curve 2804. The intensity for curve 2804 has been multiplied by 500 in FIG. 28. As can be seen from FIG. 28, a strong modification of the QD emission by the optical cavity is observed, with the enhancement in the peak intensity being of the order of 2000 times. This enhancement is higher than what would be expected from a cavity with a Q-factor of about 100 as in the example embodiment of the light emitting device. To investigate this high enhancement, in a further experiment a comparison between the photoluminescence of the example device and the same QDs deposited on the substrate Bragg mirror was made. In that experiment, the intensity enhancement was only of the order of five times, which is consistent with what would be expected for a cavity with a O-factor of about 100. This experiment suggests that the porous scaffold, i.e. the porous silicon in the example embodiment, is playing a significant role in concentrating the QDs, thus significantly contributing to the emission enhancement.

Figure 29:
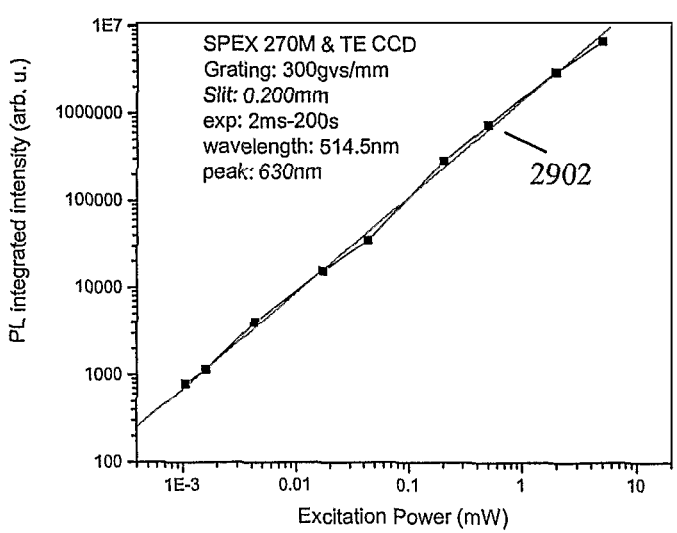
FIG. 29 shows a plot of photo luminescence intensity versus excitation intensity from 1 μW to 5 mW of the light emitting device of the example embodiment.
Figure 30:
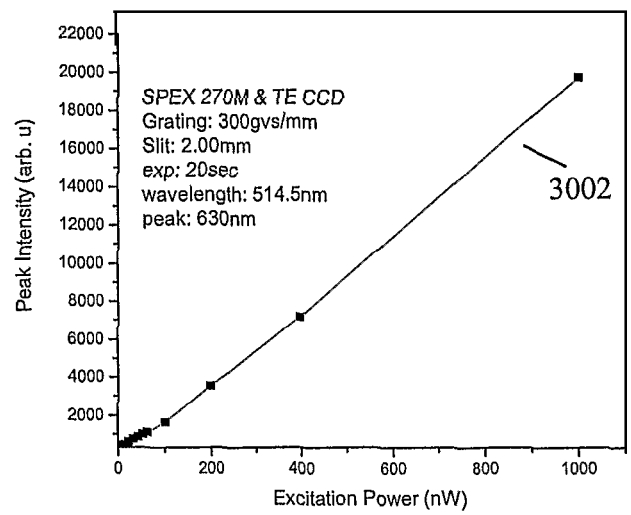
FIG. 30 shows a plot of photo luminescence intensity versus excitation intensity from 10 mW to 1 μW of the light emitting device of the example embodiment.

FIG. 29 shows a plot 2902 of photoluminescence intensity versus excitation power from 1 µW to 5 mW, and FIG. 30 shows a plot 3002 of photoluminescence intensity versus excitation power from 10 mW to 1 µW, for the example light emitting device. From FIGS. 29 and 30 it can be seen that a substantially linear trend over seven orders of magnitude was found, with no observable evidence of lasing occurring. As will be appreciated by a person skilled in the art, evidence of a lasing threshold would be observed by an exponentially increasing region.

Figure 31:
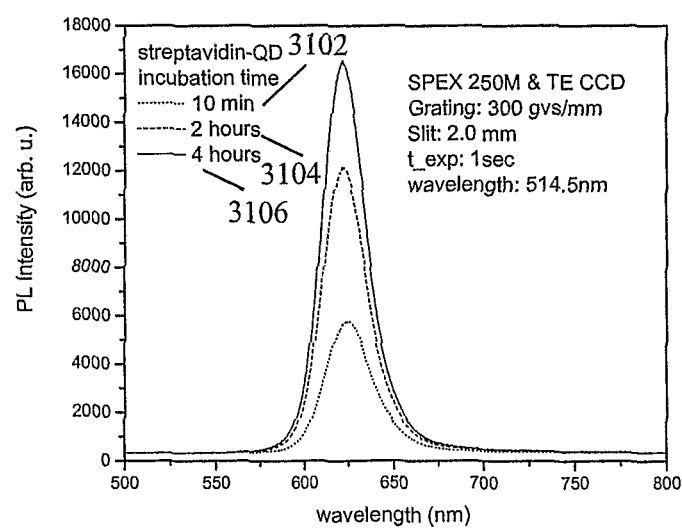
FIG. 31 shows photo luminescence intensity versus incubation time graphs for different streptavidin-QD incubation times of 10 minutes for the light emitting device of the example embodiment.

FIG. 31 shows photoluminescence intensity versus incubation time graphs for different streptavidin-QD incubation times of 10 minutes (curve 3102), 2 hours (3104), and 4 hours (curve 3106). From FIG. 31, it can be seen that increasing the incubation time increases the photo luminescence intensity, believed to be due to an increase in the number of QDs deposited.

In different embodiments, the optical device may be optimised by varying the composition of the light emitting material, including the QDs. For example, a layer by layer approach with alternately streptavidin and biotin coated QDs to form a stacked light emitting material structure may be employed to seek to optimize the performance of the light emitting device. Alternatively or additionally, different types of QDs may be incorporated, including incorporating different types of QDs in different lateral areas within a layer, incorporating different types of QDs in different layers, or both. In such embodiments, optical devices for different desired applications can be realised, e.g. multi-color light emitting devices, light emitting devices in which one or more types of QDs are optimised for absorption of the pump energy, while one or more other types of QDs are optimised for light emission through energy transfer from the QDs optimised for absorption, or absorption based optical devices including devices in which different types of QDs are configured in a photo-voltaic cell arrangement, e.g. in a p-n junction (s).

Figure 32:
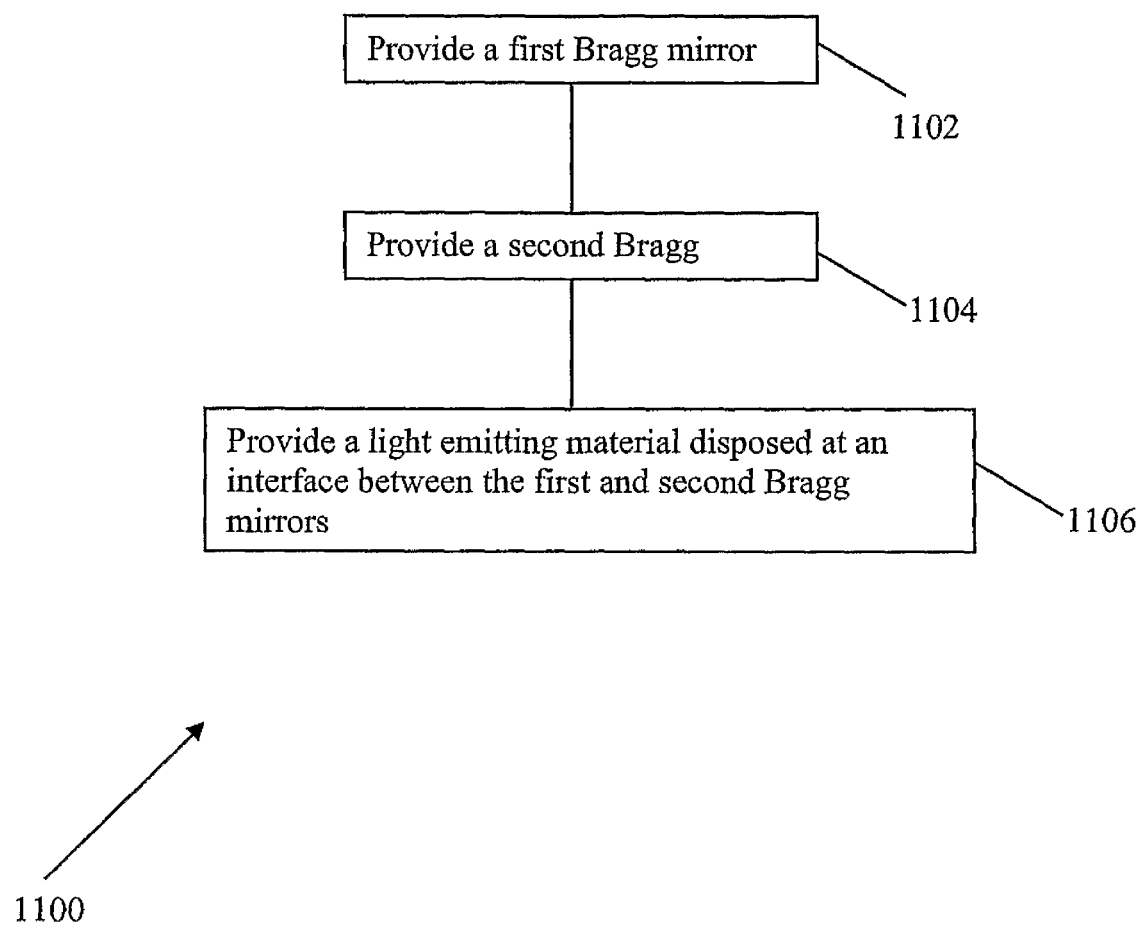
FIG. 32 shows a flow chart illustrating a method of fabricating a light emitting device according to an example embodiment.

FIG. 32 shows a flow chart 3200 illustrating a method of fabricating a light emitting device according to an example embodiment. At step 3202, a first Bragg mirror is provided. At step 3204, a second Bragg mirror is provided. At step 3206, a light emitting material disposed at an interface between the first and second Bragg mirrors is provided, wherein the second Bragg mirror is assembled on the first Bragg mirror by a binding interaction via the light emitting material.

The example light emitting device described provides a silicon integrated light emitter, which can have applications in integrated silicon based optoelectronic devices. The applicant is not aware of quantum dot doped microcavities formed using Si integrated optical epitaxial techniques having been reported before.

It will be appreciated by a person skilled in the art that numerous variations and/or modifications may be made to the present invention as shown in the specific embodiments.

For example, it will be appreciated that the light emitting device may be optically or electrically pumped, using different optical or electrical sources. Furthermore, while II-VI QDs were used in the example embodiment, it will be appreciated that other QDs may be used in different embodiments, including III-V QDs. Furthermore, a gain material may be incorporated into the light emitting material, to facilitate lasing.

Also, while a biotinylated BSA and protein avidin pair has been described, it will be appreciated that other pairs of biorecognition elements and complimentary species may be used in different embodiments.

The invention claimed is:

1. A method for fabricating a sensor structure, the method comprising the steps of:
   providing a first Bragg mirror;
   providing a second Bragg mirror as a free-standing component; and
   providing a stimuli responsive material disposed between the first and second Bragg mirrors;
   wherein the second Bragg mirror is assembled on the first Bragg mirror by a binding interaction via the stimuli responsive material.

2. The method as claimed in claim 1, wherein the first Bragg mirror is formed on a first substrate.

3. The method as claimed in claim 1, further comprising derivatizing a surface of at least one of the first and second Bragg mirrors prior to providing the stimuli responsive material disposed between the first and second Bragg mirrors.

4. The method as claimed in claim 1, wherein providing the second Bragg mirror as a free-standing component further comprises the steps of
   forming the second Bragg mirror on a further substrate; and
   lifting off the second Bragg mirror from the substrate prior to assembling the second Bragg mirror on the first Bragg mirror.

5. The method as claimed in claim 1, the method further comprising the step of anodizing crystalline silicon in ethanolic hydrofluoric acid solution with a step function to yield alternating layers of high and low refractive index with an optical thickness to form the Bragg mirrors.

6. The method of claim 1, wherein the stimuli responsive material comprises at least one of gelatin, an extracellular matrix biopolymer, a protein, an oligosaccharide, a proteoglycan, a recombinant polypeptide, a synthetic polypeptides, a nucleic acid, a synthetic co-polymer system, a small molecule and nano-object encapsulated polymer, a pNIPAM, a lipids, a carbohydrate, cellulose, a cell, plant tissue, animal tissue, a polymer, a hydrogel, a microorganisms, a nanoparticle, or a nanowire.

7. The method of claim 1, further comprising derivatizing a surface of at least one of the first and second Bragg mirrors using at least one of a succininide ester, a carboxylic acid, an amine, a maleimide, an epoxide, an azide, an alkynes, an alcohols, a carbodiimide, an aldehyde, a diazonium, an imines, an acid chloride, a disulfide, or an anhydrides.

8. The method of claim 1, wherein the stimuli responsive material is disposed between the first and second Bragg mirrors such that infiltration of the stimuli responsive material is prevented.

9. The method of claim 1, wherein a stimuli for the stimuli responsive material comprises at least one of a biomolecule, a chemical, a temperature, light, a pH, a voltage, or a mechanical force.

10. The method of claim 1, wherein providing the first and second Bragg mirrors comprises providing the first and second Bragg mirrors such that at least one of the first and second Bragg mirrors are responsive to a further stimuli.

11. The method of claim 1, wherein at least one of the first and second Bragg mirrors comprise PSi nanoporous structures.

12. A method of fabricating a light emitting device, the method comprising the steps of:
   providing a first Bragg mirror;
   providing a second Bragg mirror as a free-standing component; and
   providing a light emitting material disposed at an interface between the first and second Bragg mirrors;
   wherein the second Bragg mirror is assembled on the first Bragg mirror by a binding interaction via the light emitting material.

13. The method of claim 12, wherein the light emitting material comprises at least one of a biorecognition element, a complementary biomolecular species, and quantum dots.

14. The method of claim 12, wherein the light emitting material comprises a mixture of at least one biorecognition elements, at least one complementary biomolecular species, and quantum dots, wherein the binding interaction comprises the quantum dots being bound via pairs of the biorecognition elements and the complementary species.

15. The method of claim 14, wherein the binding interaction further comprises the at least one biorecognition elements, the at least one complementary biomolecular species, and the quantum dots diffusing into respective interfacial regions of the first and second Bragg mirrors.

16. The method of claim 14, wherein the quantum dots comprise II-VI semiconductor quantum dots or III-V semiconductor quantum dots.

17. The method of claim 12, wherein the light emitting material comprises at least one of different types of QDs in different lateral areas within a layer or different types of QDs in different layers.

18. The method of claim 12, further comprising forming an optical cavity at the interface between the first and second Bragg mirrors.

19. The method of claim 12, wherein the light emitting material further comprises a gain material for facilitating lasing.

20. The method of claim 19, wherein a thickness of the optical cavity matches an emission wavelength of the light emitting material.

* * * * *